United States Patent [19]

Skuballa et al.

[11] 4,105,792
[45] Aug. 8, 1978

[54] PROSTANE DERVATIVES

[75] Inventors: Werner Skuballa; Bernd Radüchel; Helmut Vorbrüggen; Walter Elger; Olaf Loge; Eckehard Schillinger, all of Berlin, Fed. Rep. of Germany

[73] Assignee: Schering Aktiengesellschaft, Berlin and Bergkamen, Fed. Rep. of Germany

[21] Appl. No.: 689,849

[22] Filed: May 25, 1976

[30] Foreign Application Priority Data

May 26, 1975 [DE] Fed. Rep. of Germany ....... 2523676
Apr. 12, 1976 [DE] Fed. Rep. of Germany ....... 2616304

[51] Int. Cl.$^2$ .................. C07C 69/34; C07C 177/00; A61K 31/225

[52] U.S. Cl. .................. 424/313; 560/122; 560/148; 544/383; 560/159; 560/160; 544/379; 560/161; 560/162; 544/377; 560/163; 560/164; 544/360; 560/173; 560/187; 260/293.65; 560/188; 560/193; 260/295 R; 560/194; 560/228; 260/295.5 R; 560/231; 560/255; 260/326.5 S; 424/248.5; 424/248.55; 260/340.6; 424/266; 424/267; 260/347.5; 424/274; 424/283; 260/410; 424/285; 424/300; 260/410.5; 424/303; 424/305; 260/448.2 B; 424/308; 424/311; 260/455 A; 424/312; 260/456 R; 260/456 P; 260/456 A; 260/458 C; 260/946; 260/953; 544/158; 544/171; 560/1; 560/28; 560/31; 560/32; 560/61; 560/72; 560/84; 560/106; 560/107; 560/115

[58] Field of Search .......... 260/485 L, 485 G, 475 P, 260/468 K; 424/305, 308, 313; 560/193, 194

[56] References Cited

U.S. PATENT DOCUMENTS

| 3,723,528 | 3/1973 | Pike | 260/556 A |
| 3,970,685 | 7/1976 | Untch et al. | 260/468 D |

OTHER PUBLICATIONS

Belgian 817,513 Abstract Jan. 1975.
Belgian 832,229 Abstract Dec. 1975.
German 2,502,919 Abstract Jul. 1975.

Primary Examiner—Jane S. Myers
Attorney, Agent, or Firm—Millen & White

[57] ABSTRACT

Prostan-1-ol esters and intermediates for their preparation are described; the former compounds exhibit improved organ specificity and a longer duration of activity at lower dosages than the corresponding non-esterified prostaglandins and are useful, inter alia, in triggering abortion, inducing labor and regulating the menstrual cycle.

9 Claims, No Drawings

PROSTANE DERIVATIVES

BACKGROUND OF THE INVENTION

This invention relates to novel prostane derivatives and processes for the preparation thereof.

It is known that the physiological effects of the prostaglandins in the mammalian organism as well as in vitro are only of a brief duration, since they are rapidly converted into a plurality of pharmacologically inactive metabolic products. It is furthermore known that the natural prostaglandins per se do not possess any biological specificity, which is necessary for a medicinal agent.

It is, therefore, desirable to develop prostaglandin analogs having a spectrum of activity comparable to the natural prostaglandins and to make structural changes by which the duration and selectivity of the effectiveness are increased.

It has now been found that prostan-1-ol esters exhibit surprisingly an excellent specificity of activity and a longer duration of effectiveness than natural prostaglandins. Thus, the compounds of the present invention show, for example, a very good effect on the uterus, while the intestinal musculature and the vascular musculature remain practically unaffected.

OBJECTS OF THE INVENTION

Accordingly, it is a general object of this invention to provide new prostaglandin derivatives having improved specificity and duration of physiological activity and intermediates for the preparation thereof.

Another object of this invention is to provide a series of prostan-1-ol esters which exhibit pronounced activity on uterine musculature which minimally affecting intestinal and vascular musculature.

A further object of this invention is to provide new prostaglandins of the PG A, D, E and F series useful in triggering abortion or labor and in regulating the menstrual cycle in female mammals.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing prostane derivatives of the formula

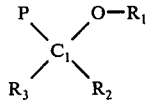

wherein

P is an arbitrarily substituted prostane nucleus linked by way of the $C_1$ carbon atom;

$R_1$ is a physiologically acceptable acid residue of an organic carboxylic or sulfonic acid of 1–15 carbon atoms or of an inorganic acid, or a physiologically acceptable

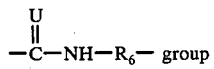

wherein U is oxygen or sulfur and $R_6$ is optionally substituted alkyl of 1–10 carbon atoms, cycloalkyl of 4–8 carbon atoms, aryl of 6–12 carbon atoms, or the acid residue of an organic carboxylic or sulfonic acid of 1–15 carbon atoms or of an inorganic acid, and $R_2$ and $R_3$ are each hydrogen or alkyl of 1–4 carbon atoms or $R_2$ is a hydrogen atom and $R_3$ is a alkyl of 1 – 3 carbon atoms.

In another aspect, intermediates useful for preparation of the above compounds are provided by the present invention of the formula:

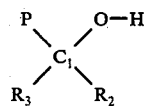

wherein

P is an arbitrarily substituted prostane nucleus linked by way of the $C_1$ carbon atom; and $R_2$ and $R_3$ equal or different and are each hydrogen or alkyl of 1–4 carbon atoms or $R_2$ is a hydrogen atom and $R_3$ is a alkyl of 1–4 carbon atoms, or $R_2$ and $R_3$ are both hydrogens.

The prostane residue P can be substituted as desired. Those prostane residues P are preferred which occur in naturally existing and synthetically prepared prostaglandins.

Possible functional groups or substituents of the prostane residue P are known and include but are not limited to alkyl groups of 1–4 carbon atoms in the 1-, 2-, 3-, 13-, 16-, 17-, 11- and/or 15-positions; aryl groups, preferably phenyl, in the 11- and/or 17-positions; alkylene groups, preferably methylene, in the 10,11- and/or 13,14-positions; hydroxy or functionally modified hydroxy groups in the 9-, 11- and/or 15-positions; oxo groups in the 9-, 11- and/or 15-positions; double bonds in the 5,6-, 10,11-, 13,14- and/or 17,18-positions; triple bonds in the 13,14-, 16,17- and/or 4,5-positions; ketals in the 15-position; halogen atoms in the 10-, 14-, 16- and/or 17-positions.

Preferred prostane derivatives of the present invention are compounds of general formula II

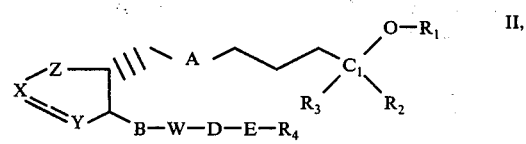

wherein $R_1$, $R_2$, and $R_3$ have the above-indicated meanings,

A represents a —$CH_2$—$CH_2$— or cis-CH=CH— or trans-CH=CH-group,

B represents a —$CH_2$—$CH_2$— or a trans-CH=CH- group or a —C≡C-group or a

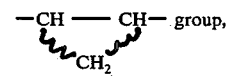

group, wherein the methylene group can be in the α- or β-position,

W represents a free or functionally modified hydroxymethylene group, a free or functionally modified carbonyl group, or a

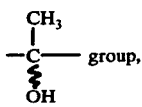 group, wherein the OH-group can be in the α- or β-position and can be functionally modified, D and E together represent a direct bond or
D represents a straight-chain or branched alkylene group of 1-5 carbon atoms or a —C≡C-group and
E represents an oxygen or sulfur atom or a direct bond,
R₄ represents an alkyl group, a cycloalkyl group, an optionally substituted aryl group, a benzodioxol-2-yl-group, or a heterocyclic group,
Z represents a carbonyl group or a free or functionally modified hydroxymethylene group, X⁼Y stands for

wherein the methylene group can be in the α- or β-position, for

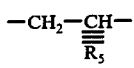

or for

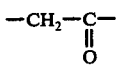

is Z represents a hydroxymethylene group, or for

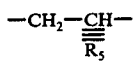

or —CH═CH— if Z represents a carbonyl group, wherein the residue R₅ is an alkyl group or a free or functionally modified hydroxy group. A

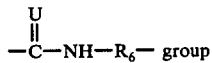

is understood to mean a substituted carbamoyl or thiocarbamoyl residue. The carbamic acid or thiocarbamic acid can be substituted on the nitrogen atom by an alkyl, cycloalkyl, aryl, or acid residue.

Suitable alkyl groups R₆ are straight-chain or branched alkyl groups of 1-10 carbon atoms, such as, for example, methyl, ethyl, propyl, isobutyl, butyl, pentyl, heptyl, hexyl, decyl, etc.

The alkyl groups R₆ can optionally be mono- to polysubstituted by halogen atoms, alkoxy groups, optionally substituted aryl groups, dialkylamines, and trialkylammonium.

Examples for suitable substituents are fluorine, chlorine, or bromine atoms, phenyl, dimethylamine, diethylamine, methoxy, ethoxy, etc.

Preferred alkyl groups R₆ are methyl, ethyl, propyl, isobutyl, butyl, trichloromethyl and trifluoromethyl.

Cycloalkyl groups R₆ are residues of 4-8 carbon atoms, such as, for example, cyclobutyl, cyclopentyl, cyclohexyl and preferably cyclopropyl.

Aryl groups R₆ can be substituted as well as unsubstituted aryl groups and heteroaryl groups, such as, for example, phenyl, 1-naphthyl, 2-naphthyl, thienyl, furyl and pyridyl, each of which can be substituted by 1 to 3 halogen atoms, a phenyl group, 1 to 3 alkyl groups of respectively 1-4 carbon atoms, a chloromethyl, fluoromethyl, trifluoromethyl or alkoxy group. Substitution in the 3- and 4-positions on the phenyl ring is preferred, for example by fluorine, chlorine, alkoxy or trifluoromethyl.

Suitable acid residues R₁ and R₆ are physiologically compatible acid residues. Preferred acids are organic carboxylic acids and sulfonic acids of 1-15 carbon atoms pertaining to the aliphatic, cycloaliphatic, aromatic, aromatic-aliphatic, or heterocyclic series. These acids can be saturated, unsaturated and/or polybasic and/or can be substituted in the usual way. Examples for substituents are alkyl, hydroxy, alkoxy, oxo or amino groups or halogen atoms.

The following carboxylic acids are suitable, for example: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert.-butylacetic acid; cyclopentylacetic acid, cyclohexylacetic acid, cyclohexanecarboxylic acid; phenylacetic acid, phenoxyacetic acid; methoxyacetic acid, ethoxyacetic acid; mono-, di-, and trichloroacetic acid; aminoacetic acid, diethylaminoacetic acid, piperidinoacetic acid, morpholinoacetic acid; lactic acid, succinic acid, adipic acid, benzoic acid; benzoic acids substituted with halogen, trifluoromethyl, hydroxy, alkoxy or carboxy groups; nicotinic acid, isonicotinic acid, furan-2-carboxylic acid, cyclopentylpropionic acid, etc. Especially preferred acyl residues are those of up to 10 carbon atoms.

Examples of suitable sulfonic acids are methanesulfonic acid, ethanesulfonic acid, isopropylsulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino, N-methylpiperazino- and morpholinosulfonic acid, etc.

Furthermore suitable for R₁ are the usual inorganic acids, e.g. sulfuric and phosphoric acid.

Alkyl groups R₂ and R₃ can be straight-chain and branched alkyl residues of 1-4 carbon atoms, such as, for example, the methyl, ethyl, propyl, isopropyl, butyl, isobutyl and tert.-butyl residues. The methyl and ethyl groups are preferred.

The hydroxy groups R₅ and those in W and Z can be functionally modified, e.g. by etherification or esterification, wherein the free or modified hydroxy groups in W and Z can be in the α- or β-position.

Suitable ether and acyl residues are those known to persons skilled in the art. Preferred are ether residues which can be readily split off, such as, for example, the tetrahydropyranyl, tetrahydrofuranyl, α-ethoxyethyl, trimethylsilyl, dimethyl-tert.-butylsilyl and tri-p-benzylsilyl residues. Acyl residues are the same as those recited for $R_1$; specific examples in this connection are acetyl, propionyl, butyryl, benzoyl, etc.

If W represents a carbonyl group, the latter can be functionally modified according to methods known to those skilled in the art, for example by ketalization. Especially advantageous is the production of cyclic ketals with 1–3 carbon atoms in the ring, such as, for example, with ethylene glycol, 1,3-propanediol, 2,2-dimethyl-1,3-propanediol, 1,2-cyclopentanediol or glycerol.

Alkyl groups $R_4$ can be straight-chain and branched, saturated and unsaturated alkyl residues, preferably saturated residues of 1–10, especially 1–6 carbon atoms, which can optionally be substituted by aryl which in turn can be substituted, if desired. Examples in this connection are methyl, ethyl, propyl, butyl, isobutyl, tert.-butyl, pentyl, hexyl, heptyl, octyl, butenyl, isobutenyl, propenyl, pentenyl, benzyl and p-chlorobenzyl.

The cycloalkyl group $R_4$ can contain 4–10, preferably 5 or 6 carbon atoms in the ring. The rings can be substituted by alkyl groups of 1–4 carbon atoms. Examples are cyclopentyl, cyclohexyl, methylcyclohexyl and adamantyl.

Examples of substituted or unsubstituted aryl groups $R_4$ are: phenyl, 1-naphthyl and 2-naphthyl, each of which can be substituted by 1–3 halogen atoms, a phenyl group, 1–3 alkyl groups of respectively 1–4 carbon atoms, a chloromethyl, fluoromethyl, trifluoromethyl, carboxy, alkoxy or hydroxy group.

Substitution in the 3- and 4-positions on the phenyl ring is preferred, for example by fluorine, chlorine, alkoxy or trifluoromethyl or, in the 4-position, by hydroxy.

Suitable alkyl residues $R_5$ are lower alkyl residues of 1–2 carbon atoms, preferably the methyl residue.

Suitable heterocyclic groups $R_4$ are 5- and 6-membered heterocyclic containing at least one hetero atom, preferably nitrogen, oxygen or sulfur. Examples are 2-furyl, 2-thienyl, 2-pyridyl, 3-pyridyl, 4-pyridyl, etc.

The invention furthermore relates to a process for the preparation of the novel prostane derivatives of general Formula I, characterized in that, in a conventional manner, compounds of general Formula III

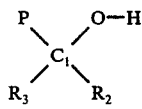   III wherein P, $R_2$, and $R_3$ have the above-indicated meanings, optionally after masking any free hydroxy groups present, are esterified in the residue P and, if desired, subsequently masked hydroxy groups are liberated and/or free hydroxy groups are oxidized or esterified and/or free keto groups are ketalized or reduced and/or double bonds are hydrogenated or the methylene group is introduced and/or, by splitting off water, a double bond is introduced into the 10,11-position, and optionally the epimers are separated.

As the preferred starting compounds, compounds of Formula IV are suitable

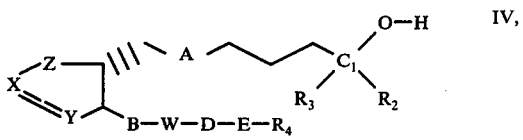

wherein $R_2$, $R_3$, A, Z, X, Y, B, W, D, E, and $R_4$ have the above-indicated meanings.

The esterification of the alcohols of general Formulae III and IV takes place as conventional. For example, the esterification is conducted by reacting an acid derivative, preferably an acid halide or acid anhydride, with an alcohol of general Formula III in the presence of a base, such as, for example, sodium hydride, pyridine, triethylamine, tributylamine or 4-dimethylaminopyridine. The reaction can be accomplished without solvents or in an inert solvent, preferably acetone, acetonitrile, dimethylacetamide or DMSO, at temperatures of above or below room temperature, e.g. between −80° and 100° C., preferably 0°–30° C. and normally at room temperature.

Furthermore, it is possible, for example, to react an alcohol of general Formula III or IV with an isocyanate or thioisocyanate of general Formula V

   V wherein U and $R_6$ have the above-indicated meanings, optionally with the addition of a tertiary amine, e.g. triethylamine or pyridine. The reaction can be carried out without a solvent or in an inert solvent, preferably acetone, acetonitrile, dimethylacetamide, methylene chloride, tetrahydrofuran, ether, benzene, toluene or DMSO, at temperatures of above or below room temperature, e.g. between −80° and 100° C., preferably at 0°–30° C.

If the starting compound contains, in addition to the OH-group in the 1-position, still other OH-groups in the prostane residue, then these OH-groups are also esterified according to the process of the present invention. If ultimate final products are desired wherein the additional hydroxy groups are present in the prostane residue as free hydroxy groups, then it is advantageous to commence the reaction with starting compounds wherein these OH-groups are blocked intermediately by preferably readily cleavable ether residues. If materials are employed as the starting compounds which carry functionally modified OH-groups, e.g., by ether formation in the prostane residue, then, after liberation of the functionally modified OH-groups in the final product, these can be esterified; it is thus possible to introduce various acyl groups into the final product.

The liberation of the functionally modified hydroxy groups takes place in accordance with known methods. For example, the splitting off of hydroxy blocking groups, such as, for instance, of the tetrahydropyranyl residue, is conducted in an aqueous solution of an organic acid, e.g. acetic acid, propionic acid, etc., or in an aqueous solution of an inorganic acid, for example hydrochloric acid or tetrabutylammonium fluoride. To improve the solubility, a water-miscible inert organic solvent is suitably utilized. Advantageous organic solvents are, for example, alcohols such as methanol and ethanol, and ethers, such as dimethoxyethane, dioxane, and tetrahydrofuran. Tetrahydrofuran is preferably employed. The splitting off reaction is preferably executed at temperatures of between 20° and 80° C.

The ketalization is conducted in a conventional manner. For example, the reaction mixture is heated with ethylene glycol in the presence of an acidic catalyst under the liberation of water. Suitable acidic catalysts are p-toluenesulfonic acid and perchloric acid, in particular.

The oxidation of any hydroxy groups present is carried out according to known methods with the customary oxidizing agents. For example, the oxidation of the 9-hydroxy group to the ketone can be attained with Jones reagent (J. Chem. Soc. 1953, 2555). The reaction is carried out with an excess of the oxidizing agent in a suitable diluent, such as acetone, at temperatures of between 0° and −50° C., preferably at −20° C. The reaction is generally terminated after 5–30 minutes. The oxidation takes place preferably after intermediately blocking the 11- and 15-hydroxy groups, e.g. by silylation (Chem. Comm. [1972] 1120). The silylation is effected, for example, with N,N-diethyltrimethylsilylamine in acetone at −70° to +20° C., preferably at −40° to 0° C. Additionally suitable oxidizing agents are silver carbonate on "Celite" or Collins reagent (Tetrahedron Letters 1968, 3363).

The regioselective oxidation of 9,11-dihydroxy compounds which do not contain an oxidizable hydroxy group in the 15-position is conducted according to methods known to those skilled in the art.

Regioselective means the selective oxidation of the 9-hydroxy group in the presence of other hydroxy groups, e.g., the 11-hydroxy groups.

For the oxidation of the 11α-hydroxy group, Jones reagent or Collins reagent is preferably employed, while the regioselective oxidation of the 9α-hydroxy group takes place with "Fetizon" reagent (Tetrahedron 29, 2867 [1973]), silver carbonate, or platinum/oxygen (Adv. in Carbohydrate Chem. 17; 169 [1962]). The oxidation with Jones reagent is carried out at −40° to +20° C., preferably at −30° to −10° C. or with Collins reagent at −20° to 30° C., preferably at 0°-20° C., in a solvent inert with respect to the oxidizing agent. Suitable solvents are methylene chloride, chloroform, ethylene chloride, pyridine and others, preferably methylene chloride.

Advantageous solvents for the oxidation with "Fetizon" reagent, silver carbonate or platinum with oxygen are benzene, toluene, xylene, ethyl acetate, acetone, tetrahydrofuran, diethyl ether, dioxane and other inert solvents. The reaction temperatures range between 20° and 110° C. in case of the silver carbonate or "Fetizon" oxidation, preferably at the boiling temperature of the solvent. When oxidizing with platinum/oxygen, temperatures of preferably 20°-50° C. are utilized.

The reduction of the 9-keto group is conducted with the usual reducing agents; for example, the reduction is carried out with sodium borohydride, lithium tri-tert-butoxyaluminum hydride, zinc borohydride, aluminum isopropylate in the presence of an alcohol or potassium tri-sec.-butyl borohydride, preferably with sodium borohydride at temperatures of between −50° and +50° C., preferably at 0°-20° C. Depending on the reducing agent employed, suitable solvents for this reaction are methanol, ethanol, isopropanol, diethyl ether, dioxane or tetrahydrofuran. When reducing with sodium borohydride, methanol, ethanol or isopropanol will preferably be used. The thus-formed α- and β-OH-epimer mixture can be separated in the usual way by column or layer chromatography.

If any C═C-double bonds present in the primary product are to be desirably reduced, the hydrogenation takes place according to conventional methods.

The hydrogenation of the 5,6-double bond is conducted conventionally at low temperatures, preferably at −20° C., in a hydrogen atmosphere in the presence of a noble metal catalyst. A suitable catalyst is, for example, 10% palladium on charcoal.

If the 5,6- as well as the 13,14-double bonds are hydrogenated, the reaction is conducted at a higher temperature, preferably at 20° C.

The dehydration of the 9-oxo compound to obtain a prostaglandin A derivative, wherein the 11-hydroxy group and a hydrogen atom from the 10-position are split off, can be carried out under conditions as generally known to a person skilled in the art. In general, the dehydration takes place in a solution of an organic acid such as acetic acid, or an inorganic acid such as hydrochloric acid, at temperatures of between 20° and 80° C. After about 2–17 hours, the reaction is terminated.

The introduction of the methylene group at the 10,11- and/or 13,14-double bond can be conducted in case of the 9-oxo or 15-oxo compound according to known methods. Examples in this connection are the reaction with diazohydrocarbons, optionally in the presence of metallic salts; the reaction with dimethyl sulfoxonium methylide; and the reaction according to Simmons-Smith with zinc and methylene dihalides.

A preferred mode of operation resides in reacting the aforementioned compounds with diazohydrocarbons, such as, for example, diazomethane, diazoethane or diazopropane, preferably with diazomethane. The reaction is conducted, for example in the presence of metallic salts, at temperatures of between b 20° and −100° C., preferably at 0° C., in an inert solvent such as, for example, diethyl ether, tetrahydrofuran, glyme, diglyme or dioxane, preferably in diethyl ether. Suitable metallic salts are copper chloride, copper acetate, palladium(II) acetate and palladium(II) chloride, preferably palladium(II) acetate.

The separation of the epimers takes place according to the methods known to those skilled in the art, such as, for example, by column or layer chromatography or by fractional crystallization.

The compounds of general Formulae III and IV, respectively, with $R_2$ and $R_3$ being hydrogen are prepared according to the usual methods, for example by reducing a corresponding prostanoic acid derivative to a primary alcohol. The reduction of prostanoic acid esters with lithium aluminum hydride is preferred.

The production of novel compounds of general Fomulae III and IV, respectively, wherein $R_2$ is an alkyl group and $R_3$ is a hydrogen atom takes place customarily, for example, by reducing a prostanoic acid derivative to the aldehyde. The reduction is preferably conducted on prostanoic acid esters with diisobutyl aluminum hydride at −70° to −40° C. in an inert solvent such as toluene, for example. The subsequent reaction of the aldehyde with alkyllithium yields, at 0° C. in an inert solvent, preferably in ether and tetrahydrofuran mixtures, the secondary alcohols of the compounds of general Formulae III and IV.

The preparation of novel compounds of general Formulae III and IV wherein $R_2$ and $R_3$ represent an alkyl group takes place according to the usual methods, for example by reacting a prostanoic acid ester with alkyllithium at temperatures of between −10° and +10° C., preferably at 0° C., in an inert solvent, such as, for example, ether and tetrahydrofuran mixtures with the formation of the tertiary alcohols of general Formulae III and IV.

If free OH-groups are desirable in the final product, it is advantageous to block intermediately any free hydroxy of free oxo groups present prior to reduction to the $C_1$-alcohols, for example by etherification or ketalization.

This invention also relates to the novel starting compounds of general Formula IIIa and especially of general Formula IVa

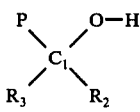  IIIa

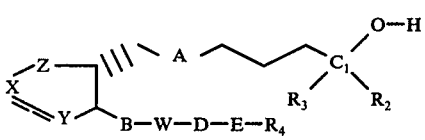  IVa wherein
P, A, Z, X, Y, B, W, D, E, and $R_4$ have the aboveindicated meanings and
$R_2$ and $R_3$ represent hydrogen or alkyl of 1–4 carbon atoms.

Preferred compounds of the present invention are those of Formulae I, II, III or IV meeting one or more of the following criteria:

(a) P is the nucleus of a prostaglandin of the A, D; E or F series, especially PG $E_2$ or PG $F_2$ or PG $A_2$;

(b) $R_1$ is alkanoyl, cycloalkanoyl, aroyl, aralkanoyl or alkylaroyl of up to 10 carbon atoms substituted by 0–3, preferably 0–2 and especially 0–1, of halogen, amino or lower alkoxy;

(c) $R_1$ is the acyl radical of a sulfonic acid corresponding to the carboxylic acids of (b);

(d) $R_1$ is the acyl radical of an inorganic acid, especially sulfuric acid or phosphoric acid;

(e) $R_1$ is

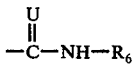

wherein $R_6$ has the preferred values set forth for $R_1$ in paragraphs (b), (c) and (d), above.

(f) $R_2$ is hydrogen, methyl or ethyl, especially hydrogen or methyl;

(g) $R_3$ is hydrogen, methyl or ethyl, especially hydrogen or methyl;

(h) $R_4$ is phenyl or substituted phenyl, especially phenyl, 3-trifluoromethyl, 4-chlorophenyl, 3-chlorophenyl, 4-fluorophenyl, 3-fluorophenyl;

(i) $R_4$ is cycloalkyl, especially cyclopentyl or cyclohexyl;

(j) $R_4$ is alkyl, especially n-pentyl, n-heptyl, hex-2-yl, 2-methyl-hex-2-yl;

(k) A is $CH_2$-$CH_2$ or cis-CH=CH- or trans-CH=CH- especially $CH_2$-$CH_2$ or cis-CH=CH-;

(l) B is $CH_2$-$CH_2$ or trans-CH=CH, or a C≡C-group or a

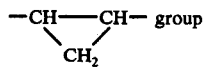

especially $CH_2$-$CH_2$ or trans-CH=CH;

(m) D and E together is a direct bond;

(n) D is alkylene, especially methylene or ethylene;

(o) E is a sulfur or oxygen atom, especially oxygen;

(p) E is a direct bond;

(q) W is a free or functionally modified hydroxymethylene group, a free or functionally modified carbonyl group or a

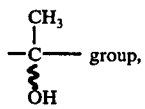

wherein the OH-group can be in the α- or β-position and can be functionally modified, especially

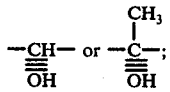

(r) Z is a carbonyl group or a free or functionally modified hydroxymethylene group especially a carbonyl group or a

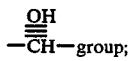

(s) X⋯Y is a

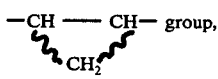

wherein the methylene group can be in the α- or β-position, especially in the α-position; (t) X⋯Y is a

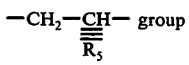

wherein the $R_5$ is alkyl or a free or functionally modified hydroxy group especially $R_5$ is methyl or hydroxy; and (u) X⋯Y is a CH=CH group or a

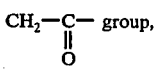

especially CH=CH.

Preferred compounds of this invention, in addition to the compounds recited in the examples, are the following:

(5Z,13E)-(8R,9S,11R,12R,15S)-1-(3-carboxypropionyloxy)-prostadiene-9,11,15-triol (5Z,13E)-(8R,11R,12R,15S)-1-(3-carboxypropionyloxy)-11,15-dihydroxyprostadien-9-one (5Z,13E)-(8R,9S,11R,12R,15S,16RS)-1-(3-carboxypropionyloxy)-16-methylprostadiene-9,11,15-triol (5Z,13E)-(8R,11R,12R,15S,16RS)-1-(3-carboxypropionyloxy)-11,15-dihydroxy-16-methylprostadien-9-one (5Z,10Z,13E)-(8R,12S,15S)-1-methoxyacetoxy-15-hydroxy-5,10,13-prostatrien-9-one (5Z,10Z,13E)-(8R,12S,15S)-1-(3-carboxypropionyloxy)-15-hydroxy-5,10,13-prostatrien-9-one (5Z,10Z,13E)-(8R,12S,15S,16RS)-1-(3-carboxypropionyloxy)-16-methyl-15-hydroxy-5,10,13-prostatrien-9-one (5Z,10Z,13E)-(8R,12S,15R)-1-(3-carboxypropionyloxy)-16,16-ethylene-15-hydroxy-5,10,13-prostatrien-9-one (10Z,13E)-(8R,12S,15S)-1-methoxyacetoxy-15-hydroxy-10,13-prostadien-9-one (10Z,13E)-(8R,12S,15S)-1-(3-carboxypropionyloxy)-15-hydroxy-10,13-prostadien-9-one (10Z,13E)-(8R,12S,15R)-1-(3-carboxypropionyloxy)-15-hydroxy-16,16-dimethyl-10,13-prostadien-9-one (10Z,13E)-(8R,12S,15S,16RS)-1-(3-carboxypropionyloxy)-15-hydroxy-16-methyl-10,13-prostadien-9-one (5Z,10Z)-(8R,12S,15S)-1-methoxyacetoxy-15-hydroxy-5,10-prostadien-9-one (5Z,10Z)-(8R,12S,15S)-1-(3-carboxypropionyloxy)-15-hydroxy-5,10-prostadien-9-one (5Z,10Z)-(8R,12S,15R)-1-(3-carboxypropionyloxy)-15-hydroxy-16,16-dimethyl-5,10-prostadien-9-one (5Z,10Z)-(8R,12S,15R,16RS)-1-(3-carboxypropionyloxy)-15-hydroxy-16-methyl-5,10-prostadien-9-one (10Z)-(8R,12S,15R)-1-(3-carboxypropionyloxy)-15-hydroxy-16,16-dimethyl-10-prosten-9-one (10Z)-(8R,12S,15R,16RS)-1-(3-carboxypropionyloxy)-15-hydroxy-16-methyl-10-prosten-9-one (5Z,13E)-(8R,9S,11R,12R,15R)-1-(3-carboxypropionyloxy)-16-phenoxy-17,18,19,20-tetranor-5,13-prostadiene-9,11,15-triol (5Z,13E)-(8R,11R,12R,15R)-1-(3-carboxypropionyloxy)-11,15-dihydroxy-16-phenoxy-17,18,19,20-tetranor-5,13-prostadien-9-one (5Z,13E)-(8R,9S,11R,12R,15R)-1-(3-carboxypropionyloxy)-16-(3-trifluoromethylphenoxy)-17,18,19,20-tetranor-5,13-prostadiene-9,11,15-triol (5Z,13E)-(8R,11R,12R,15R)-1-(3-carboxypropionyloxy)-11,15-dihydroxy-16-(3-trifluoromethylphenoxy)-17,18,19,20-tetranor-5,13-prostadien-9-one (5Z,13E)-(8R,9S,11R,12R,15R)-1-(3-carboxypropionyloxy)-16-(4-chlorophenoxy)-17,18,19,20-tetranor-5,13-prostadiene-9,11,15-triol (5Z,13E)-(8R,11R,12R,15R)-1-(3-carboxypropionyloxy)-11,15-dihydroxy-16-(4-chlorophenoxy)-17,18,19,20-tetranor-5,13-prostadien-9-one (5Z,13E)-(8R,9S,11R,12R,15R)-1-(3-carboxypropionyloxy)-16-(3-chlorophenoxy)-17,18,19,20-tetranor-5,13-prostadiene-9,11,15-triol (5Z,13E)-(8R,11R,12R,15R)-1-(3-carboxypropionyloxy)-11,15-dihydroxy-16-(3-chlorophenoxy)-17,18,19,20-tetranor-5,13-prostadien-9-one (5Z,13E)-(8R,9S,11R,12R,15R)-1-(3-carboxypropionyloxy)-16-(4-fluorophenoxy)-17,18,19,20-tetranor-5,13-prostadiene-9,11,15-triol (5Z,13E)-(8R,11R,12R,15R)-1-(3-carboxypropionyloxy)-11,15-dihydroxy-16-(4-fluorophenoxy)-17,18,19,20-tetranor-5,13-prostadiene-9,11,15-triol (5Z,13E)-(8R,9S,11R,12R,15S)-1-(N-acetylcarbamoyloxy)-5,13-prostadiene-9,11,15-triol (5Z,13E)-(8R,11R,12R,15S)-1-(N-acetylcarbamoyloxy)-11,15-dihydroxy-5,13-prostadien-9-one (5Z,13E)-(8R,12S,15S)-1-(N-acetylcarbamoyloxy)-15-hydroxy-5,10,13-prostatrien-9-one (5Z,13E)-(8R,9S,11R,12R,15S)-1-(N-phenylcarbamoyloxy)-5,13-prostadiene-9,11,15-triol (5Z,13E)-(8R,11R,12R,15S)-1-(N-phenylcarbamoyloxy)-11,15-dihydroxy-5,13-prostadien-9-one (5Z,13E)-(8R,12S,15S)-1-(N-phenylcarbamoyloxy)-15-hydroxy-5,10,13-prostatrien-9-one (5Z,13E)-(8R,9S,11R,12R,15S)-1-(N-methylthiocarbamoyloxy)-5,13-prostadiene-9,11,15-triol (5Z,13E)-(8R,11R,12R,15S)-1-(n-methylthiocarbamoyloxy)-11,15-dihydroxy-5,13-prostadien-9-one (5Z,13E)-(8R,12S,15S)-1-(N-methylthiocarbamoyloxy)-15-hydroxy-5,10,13-prostatrien-9-one (5Z,13E)-(8R,9S,11R,12R,15S)-1-(N-methylcarbamoyloxy)-15-methyl-5,13-prostadiene-9,11,15-triol (5Z,13E)-(8R,11R,12R,15S)-1-(N-methylcarbamoyloxy)-11,15-dihydroxy-15-methyl-5,13-prostadien-9-one (5Z,13E)-(8R,12S,15S)-1-(N-methylcarbamoyloxy)-15-hydroxy-15-methyl-5,10,13-prostatrien-9-one (5Z,13E)-(8R,9S,11R,12R,15S,16RS)-1-(N-methylcarbamoyloxy)-16-methyl-5,13-prostadiene-9,11,15-triol (5Z,13E)-(8R,11R,12R,15S,16RS)-1-(N-methylcarbamoyloxy)-11,15-dihydroxy-16-methyl-5,13-prostadien-9-one (5Z,13E)-(8R,12S,15S,16RS)-1-(N-methylcarbamoyloxy)-15-hydroxy-16-methyl-5,10,13-prostatrien-9-one (5Z,13E)-(8R,9S,11R,12R,15R)-1-(N-methylcarbamoyloxy)-16,16-dimethyl-5,13-prostadiene-9,11,15-triol (5Z,13E)-(8R,11R,12R,15R)-1-(N-methylcarbamoyloxy)-11,15-dihydroxy-16,16-dimethyl-5,13-prostadien-9-one (5Z,13E)-(8R,12S,15R)-1-(N-methylcarbamoyloxy)-15-hydroxy-16,16-dimethyl-5,10,13-prostatrien-9-one (5Z,13E)-(8R,9S,11R,12R,15R)-1-(N-methylcarbamoyloxy)-16-phenoxy-17,18,19,20-tetranor-5,13-prostadiene-9,11,15-triol (5Z,13E)-(8R,11R,12R,15R)-1-(N-methylcarbamoyloxy)-11,15-dihydroxy-16-phenoxy-17,18,19,20-tetranor-5,13-prostadien-9-one (5Z,13E)-(8R,9S,11R,12R,15R)-1-(N-methylcarbamoyloxy)-16-(3-trifluoromethylphenoxy)-17,18,19,20-tetranor-5,13-prostadiene-9,11,15-triol (5Z,13E)-(8R,11R,12R,15R)-1-(N-methylcarbamoyloxy)-11,15-dihydroxy-16-(3-trifluoromethylphenoxy)-17,18,19,20-tetranor-5,13-prostadien-9-one (5Z,13E)-(8R,9S,11R,12R,15R)-1-(N-methylcarbamoyloxy)-16-(4-chlorophenoxy)-17,18,19,20-tetranor-5,13-prostadiene-9,11,15-triol (5Z,13E)-(8R,11R,12R,15R)-1-(N-methylcarbamoyloxy)-11,15-dihydroxy-16-(4-chlorophenoxy)-17,18,19,20-tetranor-5,13-prostadien-9-one (5Z,13E)-(8R,9S,11R,12R,15S)-1-(N-methylcarbamoyloxy)-17-phenyl-18,19,20-trinor-5,13-prostadiene-9,11,15-triol (5Z,13E)-(8R,11R,12R,15S)-1-(N-methylcarbamoyloxy)-11,15-dihydroxy-17-phenyl-18,19,20-trinor-5,13-prostadien-9-one (5Z,13E)-(8R,11R,12R,15S)-1-(N-methylcarbamoyloxy)-15-hydroxy-11-methyl-5,13-prostadien-9-one (5Z,13E)-(8R,9S,11R,12R,15S)-1-[(N-methanesulfonyl)-carbamoyloxy]-15-methyl-5,13-prostadiene-9,11,15-triol (5Z,13E)-(8R,11R,12R,15S)-1-[(N-methanesulfonyl)-carbamoyloxy]-11,15-dihydroxy-15-methyl-5,13-prostadien-9-one (5Z,13E)-(8R,12S,15S)-1-[(N-methanesulfonyl)-carbamoyloxy]-15-hydroxy-15-methyl-5,10,13-prostatrien-9-one (5Z,13E)-(8R,9S,11R,12R,15S,16RS)-1-[(N-methanesulfonyl)-carbamoyloxy]-16-methyl-5,13-prostadiene-9,11,15-triol (5Z,13E)-(8R,11R,12R,15S,16RS)-1-[(N-methanesulfonyl)-carbamoyloxy]-11,15-dihydroxy-16-methyl-5,13-prostadien-9-one (5Z,13E)-(8R,12S,15S)-1-[(N-methanesulfonyl)-carbamoyloxy]-15-hydroxy-16-methyl-5,10,13-prostatrien-9-one (5Z,13E)-(8R,9S,11R,12R,15R)-1-[(N-methanesulfonyl)-carbamoyloxy]-16,16-dimethyl-5,13-prostadiene-9,11,15-triol (5Z,13E)-(8R,11R,12R,15R)-1-[(N-methanesulfonyl)-carbamoyloxy]-16,16-dimethyl-11,15-dihydroxy-5,13-prostadien-9-one (5Z,13E)-(8R,12S,15R)-1-[(N-methanesulfonyl)-carbamoyloxy]-15-hydroxy-16,16-dimethyl-5,10,13-prostatrien-9-one (5Z,13E)-(8R,9S,11R,12R,15R)-1-[(N-methanesulfonyl)-carbamoyloxy]-16-phenoxy-17,18,19,20-tetranor-5,13-prostadiene-9,11,15-triol (5Z,13E)-(8R,11R,12R,15R)-1-[(N-methanesulfonyl)-carbamoyloxy]-11,15-dihydroxy-16-phenoxy-17,18,19,20-tetranor-5,13-prostadien-9-one (5Z,13E)-(8R,9S,11R,12R,15R)-1-[(N-methanesulfonyl)-carbamoyloxy]-16-(3-trifluoromethylphenoxy)-17,18,19,20-tetranor-5,13-prostadiene-9,11,15-triol (5Z,13E)-(8R,11R,12R,15R)-1-[(N-methanesulfonyl)-carbamoyloxy]-11,15-dihydroxy-16-(3-trifluoromethylphenoxy)-17,18,19,20-tetranor-5,13-prostadien-9-one (5Z,13E)-(8R,9S,11R,12R,15R)-1-[(N-methanesulfonyl)-carbamoyloxy]-16-(4-chlorophenoxy)-17,18,19,20-tetranor-5,13-prostadiene-9,11,15-triol (5Z,13E)-(8R,11R,12R,15R)-1-[(N-methanesulfonyl)-carbamoyloxy]-11,15-dihydroxy-16-(4-chlorophenoxy)-17,18,19,20-tetranor-5,13-prostadien-9-one (5Z,13E)-(8R,9S,11R,12R,15R)-1-[(N-methanesulfonyl)-carbamoyl-oxy]-16-(3-chlorophenoxy)-17,18,19,20-tetranor-5,13-prostadiene-9,11,15-triol (5Z,13E)-(8R,11R,12R,15R)-1-[(N-methanesulfonyl)-carbamoyloxy]-11,15-dihydroxy-16-(3-chlorophenoxy)-17,18,19,20-tetranor-5,13-prostadien-9-one (5Z,13E)-(8R,9S,11R,12R,15R)-1-[(N-methanesulfonyl)-carbamoyloxy]-16-(4-fluorophenoxy)-17,18,19,20-tetranor-5,13-prostadiene-9,11,15-triol (5Z,13E)-(8R,11R,12R,15R)-1-[(N-methanesulfonyl)-carbamoyloxy]-11,15-dihydroxy-16-(4-fluorophenoxy)-17,18,19,20-tetranor-5,13-prostadien-9-one (5Z,13E)-(8R,9S,11R,12R,15S)-1-[(N-methanesulfonyl)-carbamoyloxy]-17-phenyl-18,19,20-trinor-5,13-prostadiene-9,11,15-triol (5Z,13E)-(8R,11R,12R,15S)-1-[(N-methanesulfonyl)-carbamoyloxy]-11,15-dihydroxy-17-phenyl-18,19,20-trinor-5,13-prostadien-9-one (5Z,13E)-(8R,11R,12R,15S)-1-[(N-methanesulfonyl)-carbamoyloxy]-11,15-dimethyl-15-hydroxy-5,13-prostadien-9-one (5Z,13E)-(8R,11R,12R,15S)-1-[(N-methanesulfonyl)-carbamoyloxy]-15-hydroxy-11-methyl-5,13-prostadien-9-one (5Z,13E)-(8R,9S,11R,12R,15S)-1-(N-acetylcarbamoyloxy)-15-methyl-5,13-prostadiene-9,11,15-triol (5Z,13E)-(8R,11R,12R,15S)-1-(N-acetylcarbamoyloxy)-11,15-dihydroxy-15-methyl-5,13-prostadien-9-one (5Z,13E)-(8R,12S,15S)-1-(N-acetylcarbamoyloxy)-15-hydroxy-15-methyl-5,10,13-prostatrien-9-one (5Z,13E)-(8R,9S,11R,12R,15S,16RS)-1-(N-acetylcarbamoyloxy)-16-methyl-5,13-prostadiene-9,11,15-triol (5Z,13E)-(8R,11R,12R,15S,16RS)-1-(N-acetylcarbamoyloxy)-11,15-dihydroxy-16-methyl-5,13-prostadien-9-one (5Z,13E)-(8R,12S,15S,16RS)-1-(N-acetylcarbamoyloxy)-15-hydroxy-16-methyl-5,10,13-prostatrien-9-one (5Z,13E)-(8R,9S,11R,12R,15R)-1-(N-acetylcarbamoyloxy)-16,16-dimethyl-5,13-prostadiene-9,11,15-triol (5Z,13E)-(8R,11R,12R,15R)-1-(N-acetylcarbamoyloxy)-11,15-dihydroxy-16,16-dimethyl-5,13-prostadien-9-one (5Z,13E)-(8R,12S,15R)-1-(N-acetylcarbamoyloxy)-15-hydroxy-16,16-dimethyl-5,10,13-prostatrien-9-one (5Z,13E)-(8R,9S,11R,12R,15R)-1-(N-acetylcarbamoyloxy)-16-phenoxy-17,18,19,20-tetranor-5,13-prostadiene-9,11,15-triol (5Z,13E)-(8R,11R,12R,15R)-1-(N-acetylcarbamoyloxy)-11,15-dihydroxy-16-phenoxy-17,18,19,20-tetranor-5,13-prostadien-9-one (5Z,13E)-(8R,9S,11R,12R,15R)-1-(N-acetylcarbamoyloxy)-16-(3-trifluoromethylphenoxy)-17,18,19,20-tetranor-5,13-prostadiene-9,11,15-triol (5Z,13E)-(8R,11R,12R,15R)-1-(N-acetylcarbamoyloxy)-11,15-dihydroxy-16-(3-trifluoromethylphenoxy)-17,18,19,20-tetranor-5,13-prostadien-9-one (5Z,13E)-(8R,9S,11R,12R,15R)-1-(N-acetylcarbamoyloxy)-16-(4-chlorophenoxy)-17,18,19,20-tetranor-5,13-prostadiene-9,11,15-triol (5Z,13E)-(8R,11R,12R,15R)-1-(N-acetylcarbamoyloxy)-11,15-dihydroxy-16-(4-chlorophenoxy)-17,18,19,20-tetranor-5,13-prostadien-9-one (5Z,13E)-(8R,9S,11R,12R,15S)-1-(N-acetylcarbamoyloxy)-17-phenyl-18,19,20-trinor-5,13-prostadiene-9,11,15-triol (5Z,13E)-(8R,11R,12R,15S)-1-(N-acetylcarbamoyloxy)-11,15-dihydroxy-17-phenyl-18,19,20-trinor-5,13-prostadien-9-one (5Z,13E)-(8R,11R,12R,15S)-1-(N-acetylcarbamoyloxy)-15-hydroxy-11-methyl-5,13-prostadien-9-one (5Z,13E)-(8R,9S,11R,12R,15S)-1-(N-phenylcarbamoyloxy)-15-methyl-5,13-prostadiene-9,11,15-triol (5Z,13E)-(8R,11R,12R,15S)-1-(N-phenylcarbamoyloxy)-11,15-dihydroxy-15-methyl-5,13-prostadien-9-one (5Z,13E)-(8R,12S,15S)-1-(N-phenylcarbamoyloxy)-15-hydroxy-15-methyl-5,10,13-prostatrien-9-one (5Z,13E)-(8R,9S,11R,12R,15S,16RS)-1-(N-phenylcarbamoyloxy)-16-methyl-5,13-prostadiene-9,11,15-triol (5Z,13E)-(8R,11R,12R,15S,16RS)-1-(N-phenylcarbamoyloxy)-11,15-dihydroxy-16-methyl-5,13-prostadien-9-one (5Z,13E)-(8R,12S,15S,16RS)-1-(N-phenylcarbamoyloxy)-15-hydroxy-16-methyl-5,10,13-prostatrien-9-one (5Z,13E)-(8R,9S,11R,12R,15R)-1-(N-phenylcarbamoyloxy)-16,16-dimethyl-5,13-prostadiene-9,11,15-triol (5Z,13E)-(8R,11R,12R,15R)-1-(N-phenylcarbamoyloxy)-11,15-dihydroxy-16,16-dimethyl-5,13-prostadien-9-one (5Z,13E)-(8R,12S,15R)-1-(N-phenylcarbamoyloxy)-15-hydroxy-16,16-dimethyl-5,10,13-prostatrien-9-one (5Z,13E)-(8R,9S,11R,12R,15R)-1-(N-phenylcarbamoyloxy)-16-phenoxy-17,18,19,20-tetranor-5,13-prostadiene-9,11,15-triol (5Z,13E)-(8R,11R,12R,15R)-1-(N-phenylcarbamoyloxy)-11,15-dihydroxy-16-phenoxy-17,18,19,20-tetranor-5,13-prostadien-9-one (5Z,13E)-(8R,9S,11R,12R,15R)-1-(N-phenylcarbamoyloxy)-16-(3-trifluoromethylphenoxy)-17,18,19,20-tetranor-5,13-prostadiene-9,11,15-triol (5Z,13E)-(8R,11R,12R,15R)-1-(N-phenylcarbamoyloxy)-11,15-dihydroxy-16-(3-trifluoromethylphenoxy)-17,18,19,20-tetranor-5,13-prostadien-9-one (5Z,13E)-(8R,9S,11R,12R,15R)-1-(N-phenylcarbamoyloxy)-16-(4-chlorophenoxy)-17,18,19,20-tetranor-5,13-prostadiene-9,11,15-triol (5Z,13E)-(8R,11R,12R,15R)-1-(N-phenylcarbamoyloxy)-11,15-dihydroxy-16-(4-chlorophenoxy)-17,18,19,20-tetranor-5,13-prostadien-9-one (5Z,13E)-(8R,11R,12R,15S)-1-(N-phenylcarbamoyloxy)-11,15-dihydroxy-17-phenyl-18,19,20-trinor-5,13-prostadien-9-one (5Z,13E)-(8R,9S,11R,12R,15S)-1-(N-phenylcarbamoyloxy)-17-phenyl-18,19,20-trinor-5,13-prostadiene-9,11,15-triol (5Z,13E)-(8R,11R,12R,15S)-1-(N-phenylcarbamoyloxy)-15-hydroxy-11-methyl-5,13-prostadien-9-one (5Z,13E)-(8R,9S,11R,12R,15S)-1-(N-methylthiocarbamoyloxy)-15-methyl-5,13-prostadiene-9,11,15-triol (5Z,13E)-(8R,11R,12R,15S)-1-(N-methylthiocarbamoyloxy)-11,15dihydroxy-15-methyl-5,13-prostadien-9-one (5Z,13E)-(8R,12S,15S)-1-(N-methylthiocarbamoyloxy)-15-hydroxy-15-methyl-5,10,13-prostatrien-9-one (5Z,13E)-(8R,11R,12R,15S,16RS)-1-(N-methylthiocarbamoyloxy)-11,15-dihydroxy-16-methyl-5,13-prostadien-9-one (5Z,13E)-(8R,12S,15S,16RS)-1-(N-methylthiocarbamoyloxy)-15-hydroxy-16-methyl-5,10,13-prostatrien-9-one (5Z,13E)-(8R,11R,12R,15R)-1-(N-methylthiocarbamoyloxy)-11,15-dihydroxy-16,16-dimethyl-5,13-prostadien-9-one (5Z,13E)-(8R,12S,15R)-1-(N-methylthiocarbamoyloxy)-15-hydroxy-16,16-dimethyl-5,10,13-prostatrien-9-one (5Z,13E)-(8R,9S,11R,12R,15R)-1-(N-methylthiocarbamoyloxy)-16-phenoxy-17,18,19,20-tetranor-5,13-prostadiene-9,11,15-triol (5Z,13E)-(8R,11R,12R,15R)-1-(N-methylthiocarbamoyloxy)-16-phenoxy-11,15-dihydroxy-17,18,19,20-tetranor-5,13-prostadien-9-one (13E)-(8R,12S,15S,16RS)-1-(N-methylcarbamoyloxy)-15-hydroxy-16-methyl-10,13-prostadien-9-one (8R,12S,15S,16RS)-1-(N-methylcarbamoyloxy)-15-hydroxy-16-methyl-10-prosten-9-one (13E)-(8R,12S,15S,16RS)-1-[(N-methanesulfonyl)-carbamoyloxy]-15-hydroxy-16-methyl-10,13-prostadien-9-one (8R,12S,15S,16RS)-1-[(N-methanesulfonyl)-carbamoyloxy]-15-hydroxy-16-methyl-10-prosten-9-one (13E)-(8R,12S,15S,16RS)-1-(N-acetylcarbamoyloxy)-15-hydroxy-16-methyl-10,13-prostadien-9-one (8R,12S,15S,16RS)-1-(N-acetylcarbamoyloxy)-15-hydroxy-16-methyl-10-prosten-9-one (13E)-(8R,12S,15R)-1-(N-methylcarbamoyloxy)-16,16-dimethyl-15-hydroxy-10,13-prostadien-9-one (8R,12S,15R)-1-(N-methylcarbamoyloxy)-16,16-dimethyl-15-hydroxy-10-prosten-9-one (13E)-(8R,12S,15R)-1-[(N-methanesulfonyl)-carbamoyloxy]-16,16-dimethyl-15-hydroxy-10,13-prostadien-9-one (8R,12S,15R)-1-[(N-methanesulfonyl)-carbamoyloxy]-16,16-dimethyl-15-hydroxy-10-prosten-9-one (10Z,13E)-(8R,12S,15R)-1-(N-acetylcarbamoyloxy)-16,16-dimethyl-15-hydroxy-10,13-prostadien-9-one (8R,12S,15R)-1-(N-acetylcarbamoyloxy)-16,16-dimethyl-15-hydroxy-10-prosten-9-one (5Z,13E)-(8R,11R,12R,15S)-1-(N-phenylcarbamoyloxy)-15-hydroxy-11,15-dimethyl-5,13-prostadien-9-one (5Z,13E)-(8R,11R,12R,15S)-1-(N-acetylcarbamoyloxy)-15-hydroxy-11,15-dimethyl-5,13-prostadien-9-one (5Z,13E)-(8R,11R,12R,15S)-1-(N-methylcarbamoyloxy)-15-hydroxy-11,15-dimethyl-5,13-prostadien-9-one (13E)-(8R,11R,12R,15S)-1-(N-methylcarbamoyloxy)-15-hydroxy-11,15-dimethyl-13-prosten-9-one.

The novel prostane derivatives of general Formulae I and II are valuable pharmaceuticals, since they exhibit, with a similar activity spectrum, an essentially stronger and above all substantially longer effectiveness than the corresponding natural prostaglandins.

The novel prostane derivatives are suitable for inducing menstruation or interrupting a pregnancy after a one-time intrauterine administration. In this connection, a therapeutic advancement is to be seen in that — besides the surprisingly good dissociation of antifertility properties — also effects on other organic systems are almost entirely prevented. The novel compounds are furthermore suitable for synchronizing the sexual cycle in female mammals such as monkeys, rabbits, cattle, pigs, humans, etc.

The good dissociation of activity of the compounds according to this invention can be seen in the investigation on other smooth-muscle organs, such as, for example, on the guinea pig ileum or on the isolated rabbit trachea, where an essentially lower stimulation can be observed than is caused by the corresponding natural prostaglandin.

The active agents of this invention pertaining to the PG E series show on the isolated rabbit trachea in vitro a bronchodilatory effect and strongly inhibit gastric acid secretion; furthermore, they have a regulating action on cardiac dysrhythmia. The novel compounds of the PG A and PG E series also lower the blood pressure and have a diuretic activity.

The active agents of this invention pertaining to the F series have a lesser bronchoconstrictive effect than natural prostaglandin $F_{2\alpha}$, which is of great advantage for thier therapeutic use.

The compounds of this invention can be employed in mixture with conventional excipients, i.e., pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers salts for influencing osmotic pressure, buffers, coloring, flavoring and/or aromatic substances and the like which do not deleteriously react with the active compounds.

For parenteral application, particularly suitable are sterile solutions, preferably oily or aqueous solutions, as well as suspensions, emulsions or implants, including suppositories. Ampoules are convenient unit dosages.

For enteral application, particularly suitable are tablets, dragees or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

For topical application, these are employed as non-sprayable forms, viscous to semi-solid or solid forms comprising a carrier indigenous to topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers, or salts for influencing osmotic pressure, etc. For topical or inhalation application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon. Usually, the active compounds of the invention are incorporated in topical formulations in a concentration of about 0,01 to 1 weight percent.

The effective agents of this invention are employed in conjunction with the auxiliary agents known and customary in galenic pharmacy, for example, for the production of preparations to trigger abortion, to regulate the female menstrual cycle or to induce labor. For this purpose, sterile aqueous solutions containing 0.01 – 10 $\mu$g/ml. of the active compound can be used as an intravenous infusion. To produce aqueous isotonic solutions, the compounds of general Formulae I and II are especially well suitable. Alcohols, such as ethanol, ethylene glycol and propylene glycol, can be added to increase the solubility.

The compounds of this invention are generally administered to animals, including but not limited to mammals, e.g., experimental laboratory animals, livestock, household pets and humans. An abortion triggering effective daily dosage of the active compounds as administered subcutaneously to gravid rats generally comprises about 0,01 to 1, preferably 0,01 to 0,1 mg/kg., together with 1 – 2 ml. of pharmaceutically acceptable carrier.

Administration by intravenous infusion is preferred, the compounds of this invention being particularly valuable in the treatment of mammals to trigger abortion, induce labor or regulate the menstrual cycle. In this cycle, they can be employed in substantially the same manner as the known prostaglandin compounds of the PG A, PG E and PG F series.

It will be appreciated that the actual preferred amounts of active compounds used will vary according to the specific compound being utilized, the particular compositions formulated, the mode of application and the particular situs and organism being treated. Optimal application rates for a given set of conditions can be ascertained by those skilled in the art using conventional dosage determination tests in view of the above guidelines.

The compounds of Formulae III and IV are useful as intermediates in the production of compounds of Formulae I and II by modification of the free hydroxyl group.

The novel prostaglandin derivatives of the E, D and F type have a very strong luteolytic effect, i.e., to trigger luteolysis requires essentially lower doses than in case of the corresponding natural prostaglandins.

Also for the triggering of abortions, substantially lower amounts of the novel prostaglandin derivatives are necessary as compared to the natural prostaglandins. The investigations were carried out on gravid rats and guinea pigs according to the customary methods. Thus, gravid rats were treated subcutaneously with the compounds of this invention starting with the fourth to the seventh day of pregnancy. On the ninth day, the animals were sacrificed and the uteri examined for locations of implantation. As shown by the following table, using compounds 1-7 as examples, the compounds of the present invention exhibit, in a 3- to 100-fold lower dosage, just as high an abortive activity as compared to 1 mg. per animal of PG $F_{2\alpha}$. Also, for example, (5Z,13E)-(8R,11R,12R,15R)-1-acetoxy-11,15-dihydroxy-16-phenoxy-17,18,19,20-tetranor-prostadiene-9-one, as compared to 1 mg. per animal of PG $E_2$, has the same abortive effectiveness in a dose which is 100-fold less.

TABLE

| | Compound Examined | Relative Effect (PG $F_{2\alpha}$ = 1) on Abortion in Rats |
|---|---|---|
| 1 | (5Z,13E-(8R,9S,11R,12R,15R)-1-Acetoxy-16-phenoxy-17,18,19,-20-tetranorprostadiene-9,11,15-triol | 100 |
| 2 | (5Z,13E)-(8R,9S,11R,12R,15S)-1-Acetoxy-15-methylprostadiene-9,11,15-triol | 10 |
| 3 | (5Z,13E)-(8R,9S,11R,12R,15S)-1-Acetoxy-17-phenyl-18,19,20-trinorprostadiene-9,11,15-triol | 5 |
| 4 | (5Z,13E)-(8R,9S,11R,12R,15S)-1-Acetoxyprostadiene-9,11,15-triol | 3 |
| 5 | (5Z,13E)-(8R,9S,11R,12R,15R)-1-Acetoxy-16,16-dimethyl-prostadiene-9,11,15-triol | 3 |
| 6 | (5Z,13E)-(8R,9S,11R,12R,15S)-1[(Methoxy)-acetoxy]-prostadiene-9,11,15-triol | 3 |
| 7 | (5Z,13E)-(8R,9S,11R,12R,15S)-1-Isobutyryloxyprostadiene-9,11,15-triol | 3 |

When recording the isotonic uterus contraction on narcotized rats and on the isolated rat uterus, it is found that the compounds of the present invention are substantially more effective and their duration of effectiveness is longer than in case of the corresponding natural prostaglandins.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, the temperatures are set forth uncorrected in degrees Celsius; unless otherwise indicated, all parts and percentages are by weight.

EXAMPLE 1

(5Z,13E)-(8R,9S,11R,12R,15S)-1-Acetoxyprostadiene-9,11,15-triol

A mixture of 550 mg. of (5Z,13E)-(8R,9S,11R,12R,15S)-9,11,15-tris(tetrahydropyran-2-yloxy) prostadien-1-ol, 2.5 ml. of pyridine, and 1 ml. of acetic anhydride was allowed to stand for 14 hours at room temperature. The mixture was then evaporated under vacuum, thus obtaining 600 mg. of (5Z,13E)-(8R,9S,11R,12R,15S)-1-acetoxy-9,11,15-tris(tetrahydropyran-2-yloxy) prostadiene as a light-yellow oil.

IR (CHCl$_3$): 1738, 1240 cm$^{-1}$.

The thus-obtained 1-acetate was agitated for 4 hours at 50° with 15 ml. of a mixture of acetic acid/water/tetrahydrofuran (65/35/10), evaporated under vacuum, and the residue purified by column chromatography on silica gel. With ether/ethyl acetate (8+2), 290 mg. of the title compound was obtained as a colorless oil.

IR (CHCl$_3$): 3600, 3430 (wide), 3000, 2930, 2860, 1738, 1240, 972 cm$^{-1}$.

NMR (CDCl$_3$): δ : 5.3–5.6 (4H,m); 4.06 (2H,t,J=6.5 Hz); 3.85–4.28 (3H,m); 8.05 (3H,s); 0.90 (3H,t,J=7 Hz).

The starting material for the above compound was prepared as follows:

(a) Methyl Ester of Prostaglandin F$_{2\alpha}$-9,11,15-Tris(tetrahydropyran-2-yl)-ether At 5°, 0.45 ml. of dihydropyran and 2 mg. of p-toluenesulfonic acid were added to a solution of 153 mg. of PG F$_{2\alpha}$-methyl ester in 6 ml. of methylene chloride. The mixture was stirred for 30 minutes at 0°, then poured on 3 ml. of saturated sodium bicarbonate solution, diluted with ether, the organic phase shaken twice with water, dried over magnesium sulfate, and evaporated under vacuum. After filtering the residue of the evaporation over silica gel, 216 mg. of the title compound was obtained with ether/hexane (1+1) as a colorless oil.

TLC (ether/hexane 7 + 3): Rf value 0.75.

(b) (5Z,13E)-(8R,9S,11R,12R,15S)-9,11,15-Tris(tetrahydropyran-2-yloxy)prostadien-1-ol At 10°, a solution of 1 g. of the compound prepared according to Example 1(a) in 25 ml. of ether was added dropwise to a suspension of 500 mg. of lithium aluminum hydride in 25 ml. of ether. The mixture was agitated for 1.5 hours at room temperature. Then, the excess lithium aluminum hydride was decomposed by the dropwise addition of ethyl acetate, 2 ml. of water was added, and the mixture was stirred for 45 minutes at room temperature, whereupon the mixture was filtered and evaporated under vacuum. After filtration of the residue over silica gel, 880 mg. of the title compound was produced with hexane/ether (3+2) as a colorless oil.

IR (CHCl$_3$): 3600, 3430 (wide), 3000, 2938, 2860, 1600, 975 cm$^{-1}$.

NMR (DMSO-d$_6$): δ : 5.2–5.55 (4H,m); 4.45–4.73 (3H,m); 4.3 (1,t,J=5 Hz); 0.88 (3H,t,J=7 Hz).

EXAMPLE 2

(5Z,13E)-(8R,9S,11R,12R,15S)-1-Isobutyloxyprostadiene9,11,15-triol

A mixture of 300 mg. of the compound prepared according to Example 1(b), 2 ml. of pyridine, and 0.5 ml. of isobutyric acid chloride was stirred for 14 hours at room temperature under argon. The mixture was then evaporated under vacuum, thus obtaining as the crude product (5Z,13E)-(8R,9S,11R,12R,15S)-1-isobutyryloxy-9,11,15-tris(tetrahydropyran-2-yloxy)-prostadiene in the form of a yellowish oil which was agitated without any further purification with 7 ml. of a mixture of acetic acid/water/tetrahydrofuran (65/35/10) for 5 hours at 50°. After evaporation and chromatography of the residue on silica gel, ether/ethyl acetate (8+2) yielded 160 mg. of the title compound as a colorless oil.

IR (CHCl$_3$): 3600, 3430 (wide), 2938, 2860, 1725, 1160, 973 cm$^{-1}$.

NMR (CDCl$_3$): δ : 5.23–5.56 (4H,m); 4.05 (2H,t,J=7 Hz); 3.8–4.45 (3H,m); 1.16 (6H,d,J=7 Hz); 0.90 (3H,t,J=6.5 Hz).

EXAMPLE 3

(5Z,13E)-(8R,9S,11R,12R,15S)-1-Benzoyloxyprostadiene-9,11,15-triol

A mixture of 500 mg. of the compound produced according to Example 1(b), 2 ml. of pyridine, and 0.5 ml. of benzoyl chloride was agitated for 14 hours under argon at room temperature. The mixture was then combined with 5 ml. of water, stirred for 2 hours at room temperature, extracted three times with ether, the organic extract was shaken twice with saturated sodium bicarbonate solution, twice with water, and then dried over magnesium sulfate and evaporated under vacuum, thus obtaining 545 mg. of (5Z,13E)-(8R,9S,11R,12R,15S)-1-benzoyloxy-9,11,15-tris(tetrahydropyran-2-yloxy)prostadiene as a colorless oil which was entirely uniform as per thin-layer chromatography.

TLC (ether/hexane 7+3): Rf value 0.78.

The thus-obtained 1-benzoate was agitated for 5 hours at 50° with 15 ml. of a mixture of glacial acetic acid/water/tetrahydrofuran (65/35/10), evaporated under vacuum, and the residue was purified by preparative layer chromatography on silica gel plates with ether/dioxane (7+3) as the eluent. Yield: 254 mg. of the title compound in the form of colorless crystals; m.p. 42°.

TLC (ether/dioxane 8+2): Rf value 0.27.

IR (CHCl$_3$): 3600, 3420 (wide), 3000, 2938, 2860, 1710, 1600, 1278, 970 cm$^{-1}$.

NMR (CDCl$_3$): δ : 7.4–7.6 (3H,m); 7.93–8.09 (2H,m); 5.25–5.58 (4H,m); 4.31 (2H,t,J=7 Hz); 0.90 (3H,t,J=7 Hz).

EXAMPLE 4

(5Z,13E)-(8R,9S,11R,12R,15S)-1-Butyryloxyprostadiene9,11,15-triol

A mixture of 300 mg. of the compound prepared according to Example 1(b), 2 ml. of pyridine, and 0.5 ml. of butyric anhydride was allowed to stand for 14 hours at room temperature. After evaporation, the thus-obtained crude product was (5Z,13E)-(8R,9S,11R,12R,15S)-1-butyryloxy-9,11,15-tris(tetrahydropyran-2-yloxy)prostadiene as a light-yellow oil. The latter product was stirred without further purification with 7 ml. of a mixture of glacial acetic acid/water/tetrahydrofuran (65/35/10) for 4 hours at 50°. After evaporation and chromatography of the residue on silica gel, 172 mg. of the title compound was obtained with ether/ethyl acetate (8+2) in the form of a colorless oil.

IR (CHCl$_3$): 3600, 3430 (wide), 3000, 2930, 2860, 1737, 972 cm$^{-1}$.

EXAMPLE 5

(5Z,13E)-(8R,9S,11R,12R,15S)-1-Decanoyloxyprostadiene9,11,15-triol

A mixture of 200 mg. of the compound prepared according to Example 1(b), 1.4 ml. of pyridine, and 0.4 ml. of decanoic acid chloride was allowed to stand for 14 hours at room temperature, then mixed with 0.2 ml. of water, allowed to stand for another 2 hours, diluted with 50 ml. of water, and extracted three times with respectively 30 ml. of ether. The organic phase was shaken in succession with saturated sodium bicarbonate solution and brine, dried over magnesium sulfate, and evaporated to dryness under vacuum. The thus-obtained (5Z,13E)-(8R,9S,11R,12R,15S)-1-decanoyloxy-9,11,15-tris(tetrahydropyran-2-yloxy)-prostadiene was stirred for 5 hours at 50° with 5 ml. of a mixture of glacial acetic acid/water/tetrahydrofuran (65/35/10). After evaporation, the reaction mixture was chromatographed on silica gel with ether/ethyl acetate (9+1), thus obtaining 150 mg. of the title compound as a colorless oil.

IR (CHCl$_3$): 3600, 3430 (wide), 2930, 2860, 1730, 970 cm$^{-1}$.

EXAMPLE 6

(5Z,13E)-(8R,9S,11R,12R,15S)-1-[(Methoxy)acetoxy]-prostadiene-9,11,15-triol

A mixture of 310 mg. of the compound produced according to Example 1(b), 2 ml. of pyridine, and 0.5 ml. of methoxyacetic acid chloride was agitated for 13 hours at room temperature under argon. The mixture was then evaporated under vacuum, thus obtaining as the crude product (5Z,13E)-(8R,9S,11R,12R,15S)-1-(methoxy)-acetoxy-9,11,15-tris(tetrahydropyran-2-yloxy)prostadiene as a yellowish oil which was agitated without further purification with 7 ml. of a mixture of glacial acetic acid/water/tetrahydrofuran (65/35/10) for 5 hours at 48°. Evaporation and chromatography of the residue on silica gel yielded, with ether/ethyl acetate (7+3), 158 mg. of the title compound as a colorless oil.

IR (CHCl$_3$): 3600, 3435 (wide), 3000, 2930, 2865, 1740, 975 cm$^{-1}$.

EXAMPLE 7

(5Z,13E)-(1RS,8R,9S,11R,12R,15S)-1-Acetoxy-1-methylprostadiene-9,11,15-triol

A mixture of 700 mg. of (5Z,13E)-(1RS,8R,9S,11R,12R,-15S)-1-methyl-9,11,15-tris(tetrahydropyran-2-yloxy)prostadienl-ol, 3.7 ml. of pyridine, and 1.5 ml. of acetic anhydride was allowed to stand at room temperature for 14 hours. The mixture was evaporated under vacuum, thus obtaining 770 mg. of (5Z,13E)(1RS,8R,9S,11R,12R,15S)-1-acetoxy-1-methyl-9,11,15-tris(tetrahydropyran-2-yloxy)prostadiene as a colorless oil; this product was uniform as determined by thin-layer chromatography.

TLC (ether/hexane 7+3): Rf value 0.73.

IR (CHCl$_3$): 3000, 2940, 2860, 1727, 1255, 978 cm$^{-1}$.

The thus-obtained 1-acetate was agitated for 14 hours at room temperature with 20 ml. of a mixture of glacial acetic acid/water/tetrahydrofuran (65/35/10), evaporated under vacuum, and the residue purified by column chromatography on silica gel. With ether/ethyl acetate (8+2), 385 mg. of the title compound was obtained as a colorless oil.

TLC (ether/dioxane 8+2): Rf value 0.29.

IR (CHCl$_3$): 3600, 3430 (wide), 3000, 2930, 2860, 1727, 1255, 978 cm$^{-1}$.

The starting material for the above compound was prepared as follows:

(a)

(5Z,13E)-(8R,9S,11R,12R,15S)-9,11,15Tris(tetrahydropyran-2-yloxy)prostadien-1-al 12 ml. of a 20% solution of diisobutyl aluminum hydride in toluene was added dropwise to a solution, cooled to −65°, of 1.68 g. of the compound prepared according to Example 1(a) in 80 ml. of toluene; the mixture was stirred for 15 minutes at −65°, the excess reagent was destroyed by the dropwise addition of isopropanol, 6 ml. of water was added, and the mixture was allowed to warm up to 5°. The mixture was then agitated for 1 hour, filtered off from the precipitate, and the filtrate was evaporated to dryness under vacuum, thus obtaining 1.68 g. of the title compound as a colorless oil.

TLC (ether/hexane 7+3): Rf value 0.68.

IR (CHCl$_3$): 3000, 2942, 2860, 2730, 1721, 968 cm$^{-1}$.

NMR (DMSO-d$_6$): δ : 9.63 (1H,t,J=2 Hz); 5.15–5.55 (4H,m); 4.38–4.73 (3H,m); 0.85 (3H,t,J=6.5 Hz).

(b)

(5Z,13E)-(1RS,8R,9S,11R,12R,15S)-1-Methyl-9,11,15-tris(tetrahydropyran-2-yloxy)prostadien1-ol At 0° under argon, 2.84 ml. of an approximately 2-molar solution of methyllithium in ether was added to a solution of 1.68 g. of the aldehyde obtained according to Example 7(a) in 57 ml. of ether and 57 ml. of tetrahydrofuran. The mixture was agitated for 20 minutes at 0°, then 50 ml. of saturated ammonium chloride solution was added thereto, the mixture was extracted three times with ether, the organic extract was shaken twice with water, dried over magnesium sulfate, and evaporated under vacuum, thus obtaining 1.61 g. of the title compound as a colorless oil.

TLC (ether/hexane 7+3): Rf value 0.24.

IR: 3600, 3450, 3000, 2940, 2860, 978 cm$^{-1}$.

EXAMPLE 8

(5Z,13E)-(8R,9S,11R,12R,15S)-1-Acetoxy-1,1-dimethylprostadiene-9,11,15-triol

A solution of 980 mg. of (5Z,13E)-(8R,9S,11R,12R,15S)-1,1-dimethyl-9,11,15-tris(tetrahydropyran-2-yloxy)prostadien-1-ol in 30 ml. of methylene chloride was combined with 296 mg. of 4-dimethylaminopyridine and 2.3 ml. of acetic anhydride and allowed to stand for 4 days at room temperature. After evaporation under vacuum, the residue was filtered with hexane/ether (1+1) over silica gel, thus producing 985 mg. of (5Z,13E)-(8R,9S,11R,12R,15S)-1-acetoxy-1,1-dimethyl-9,11,15-tris(tetrahydropyran-2-yloxy)-prostadiene as a colorless oil.

TLC (ether/hexane 7+3): Rf value 0.75.

IR (CHCl$_3$): 3000, 2940, 2860, 1723, 1260, 978 cm$^{-1}$.

The thus-obtained 1-acetate was agitated with 18 ml. of a mixture of acetic acid/water/tetrahydrofuran (65/35/10) for 14 hours at 25° and then evaporated under vacuum. The residue was purified by column chromatography on silica gel. With the aid of ether- /ethyl acetate (8+2), 380 mg. of the title compound was produced as a colorless oil.

IR (CHCl$_3$): 3600, 3440 (wide), 3000, 2935, 2860, 1724, 1260, 978 cm$^{-1}$.

NMR (CDCl$_3$): δ : 5.2–5.6 (4H,m); 3.8–4.3 (3H,m); 1.98 (3H,s); 1.42 (6H,s); 0.88 (3H,t,J=7 Hz).

The starting material for the above compound was prepared as follows:

(a)

(5Z,13E)-(8R,9S,11R,12R,15S)-1,1-Dimethyl-9,11,15-tris(tetrahydropyran-2-yloxy)prostadien-1-ol At 0°, a solution of 1.47 g. of the compound produced according to Example 1(a) in 48 ml. of ether and 48 ml. of tetrahydrofuran was combined under argon with 7 ml. of a 2-molar solution of methyllithium in ether. After 20 minutes, the reaction mixture was diluted with ether, shaken with saturated NaCl solution, dried with magnesium sulfate, and evaporated under vacuum, thus obtaining 1.53 g. of the title compound as a colorless oil.

TLC (ether/hexane 7+3): Rf value 0.31.

IR (CHCl$_3$): 3600, 3430 (wide), 3000, 2940, 2860, 978 cm$^{-1}$.

EXAMPLE 9

(5Z,13E)-(8R,9S,11R,12R,15S)-1-Acetoxy-15-methyl-prostadiene-9,11,15-triol

A mixture of 310 mg. of (5Z,13E)-(8R,9S,11R,12R,15S)-15-methyl-9,11,15-tris(tetrahydropyran-2-yloxy)prostadien-1-ol, 2 ml. of pyridine, and 0.5 ml. of acetic anhydride was allowed to stand for 14 hours at room temperature. The mixture was evaporated under vacuum, thus obtaining as the crude product (5Z,13E)-(8R,9S,11R,12R,15S)-1-acetoxy-15-methyl-9,11,15-tris(tetrahydro pyran-2-yloxy)prostadiene as a yellowish oil.

IR (CHCl$_3$): 1738, 1240, 975 cm$^{-1}$.

The thus-produced 1-acetate was agitated for 14 hours at room temperature with 8 ml. of a mixture of glacial acetic acid/water/tetrahydrofuran (65/35/10), evaporated under vacuum, and the residue purified by chromatography on silica gel. With ether/ethyl acetate (8+2), 152 mg. of the title compound was obtained as a colorless oil.

IR: 3595, 3430 (wide), 3000, 2935, 2860, 1738, 1240, 975 cm$^{-1}$.

The starting material for the above compound was produced as set forth below:

(a) Methyl Ester of (15S)-15-Methyl-prostaglandin-F$_{2\alpha}$-9,11,15-tris(tetrahydropyran-2-yl)ether At 5°, a solution of 160 mg. of (15S)-15-methyl-PG F$_{2\alpha}$-methyl ester [Journal of the American Chemical Society 96 (18) 5865 (1974)] in 6 ml. of methylene chloride was combined with 0.5 ml. of dihydropyran (freshly distilled) and 2 mg. of p-toluenesulfonic acid. The mixture was agitated for 30 minutes at 5°, then introduced into 4 ml. of saturated sodium bicarbonate solution, diluted with ether, and the organic phase shaken twice with water. The mixture was dried over magnesium sulfate and evaporated under vacuum. After filtration of the residue from the evaporation over silica gel, 210 mg. of the title compound was obtained as a colorless oil with ether/hexane (1+1).

TLC (ether/hexane 7+3): Rf value 0.78.

IR (CDCl$_3$): 1736, 975 cm$^{-1}$.

(b)

(5Z,13E)-(8R,9S,11R,12R,15S)-15-Methyl-9,11,15-tris(tetrahydropyran-2-yloxy)prostadien-1-ol At 5°, a solution of 0.2 g. of the compound prepared according to Example 9(a) in 5 ml. of ether was added dropwise to a suspension of 100 mg. of lithium aluminum hydride in 5 ml. of ether; the mixture was agitated for 2 hours at 22°. Thereafter, the excess lithium aluminum hydride was decomposed by the dropwise addition of ethyl acetate, 0.5 ml. of water was added, and the mixture stirred for 40 minutes at room temperature. The mixture was then filtered and evaporated under vacuum. After filtering the residue over silica gel, 177 mg. of the title compound was obtained as a colorless oil with hexane/ether (3+2).

IR (CHCl$_3$): 3600, 3430 (wide), 2998, 2940, 2860, 976 cm$^{-1}$.

EXAMPLE 10

(5Z,13E)-(8R,9S,11R,12R,15R)-1-Acetoxy-16-phenoxy-17,18,19,20-tetranorprostadiene-9,11,15-triol A mixture of 195 mg. of (5Z,13E)-(8R,9S,11R,12R,15S)-16-phenoxy-9,11,15-tris(tetrahydropyran-2-yloxy)-17,18,19,20-tetranorprostadien-1-ol, 1 ml. of pyridine, and 0.5 ml. of acetic anhydride was allowed to stand for 14 hours at room temperature. The mixture was evaporated under vacuum, thus obtaining 206 mg. of (5Z,13E)-(8R,9S,11R,12R,15R)-1-acetoxy-16-phenoxy-9,11,15-tris(tetrahydropyran-2-yloxy)prostadiene as a colorless oil.

IR (CHCl$_3$): 3000, 2936, 2860, 1728, 1600, 1588, 1495, 1240, 973 cm$^{-1}$.

The thus-obtained 1-acetate was agitated for 14 hours at room temperature with 8 ml. of a mixture of glacial acetic acid/water/tetrahydrofuran (65/35/10), evaporated under vacuum, and the residue purified by layer chromatography on silica gel plates. With ether/dioxane (8+2), 72 mg. of the title compound was produced as a colorless oil.

IR (CHCl$_3$): 3595, 3440, 3000, 2940, 2860, 1728, 1600, 1588, 1495, 1240, 975 cm$^{-1}$.

The starting material for the above compound was prepared as follows:

(a)

(5Z,13E)-(8R,9S,11R,12R,15R)-16-Phenoxy-9,11,15-tris(tetrahydropyran-2-yloxy)-17,18,19,20-tetranorprostadienoic Acid Methyl Ester At 5°, 0.14 ml. of dihydropyran and 1.5 mg. of p-toluenesulfonic acid were added to a solution of 140 mg. of the methyl ester of (5Z,13E)-(8R,9S,11R,12R,15R)-16-phenoxy-9,11,15-trihydroxy-17,18,19,20-tetranorprostadienoic acid (see DOS's [German Unexamined Laid-Open Applications] 2,223,365 and 2,322,673) in 4.5 ml. of methylene chloride. The mixture was agitated for 30 minutes at 5°, poured on 4 ml. of saturated sodium bicarbonate solution, diluted with ether, the organic phase shaken twice with water, dried over magnesium sulfate, and evaporated under vacuum. Filtration of the residue over silica gel yielded, with ether/hexane (1+1), 205 mg. of the title compound as a colorless oil.

TLC (ether/hexane 7+3): Rf value 0.71.

(b)

(5Z,13E)-(8R,9S,11R,12R,15R)-16-Phenoxy-9,11,15-tris(tetrahydropyran-2-yloxy)-17,18,19,20-tetranorprostadien-1-ol At 5°, a solution of 238 mg. of the compound prepared according to Example 10(a) in 7 ml. of ether was added dropwise to a suspension of 122 mg. of lithium aluminum hydride in 7 ml. of ether. The mixture was agitated for 2 hours at room temperature. Thereafter, the excess reagent was destroyed by the dropwise addition of ethyl acetate, 0.8 ml. of water was added thereto, and the mixture was stirred for 40 minutes at room temperature and then filtered and evaporated under vacuum. After filtration of the residue over silica gel, 196 mg. of the title compound was obtained as a colorless oil with ether/hexane (3+2).

IR (CHCl$_3$): 3600, 3430, 3000, 2940, 2860, 1600, 1588, 1495, 975 cm$^{-1}$.

EXAMPLE 11

By proceeding in accordance with Example 10, but with the use of the methyl ester of (5Z,13E)-(8R,9S,11R,12R,15R)-16-(3-trifluoromethylphenoxy)-9,11,15-trihydroxy-17,18,19,20-tetranorprostadienoic acid (see DOS's 2,223,365 and 2,322,673), one obtains (5Z,13E)-(8R,9S,11R,12R,15R)-1-acetoxy-16-(3-trifluoromethylphenoxy)-17,18,19,20-tetranorprostadiene-9,11,15-triol as a colorless oil.

IR (CHCl$_3$): 3600, 3430, 3000, 2940, 2860, 1730, 1600, 1592, 1490, 1240, 975 cm$^{-1}$.

EXAMPLE 12

By following the procedure of Example 10, but using the methyl ester of (5Z,13E)-(8R,9S,11R,12R,15R)-16-(4-chlorophenoxy)-9,11,15-trihydroxy-17,18,19,20-tetranorprostadienoic acid (see DOS's 2,223,365 and 2,322,673), then (5Z,13E)-(8R,9S,11R,12R,15R)-1-acetoxy-16-(4-chlorophenoxy)-17,18,19,20-tetranorprostadiene-9,11,15-triol is produced as a colorless oil.

IR (CHCl$_3$): 3600, 3430 (wide), 3000, 2950, 2860, 1730, 1600, 1583, 1492, 1245, 975, 872, 828 cm$^{-1}$.

EXAMPLE 13

Proceeding analogously to Example 10, but using the methyl ester of (5Z,13E)-(8R,9S,11R,12R,15S)-17-phenyl-9,11,15-trihydroxy-18,19,20-trinorprostadienoic acid (see DOS 2,234,709), the product is (5Z,13E)-(8R,9S,11R,12R,15S)-1-acetoxy-17-phenyl-18,19,20-trinorprostadiene-9,11,15-triol in the form of a colorless oil.

IR (CHCl$_3$): 3600, 3400 (wide), 3000, 2960, 2860, 1732, 1600, 1250, 975 cm$^{-1}$.

EXAMPLE 14

By following the method of Example 10, but employing the methyl ester of (5Z,13E)-(8R,9S,11R,12R,15S)-9,15-dihydroxy-11-methyl-prostadienoic acid (see Chemistry and Industry 1973, 635), (5Z, 13E)-(8R,9S,11R,12R,15S)-1-acetoxy-11-methylprostadiene-9,15-diol is obtained as a colorless oil.

IR (CHCl$_3$): 3600, 3430, 3000, 2950, 2860, 1725, 1260, 978 cm$^{-1}$.

EXAMPLE 15

By following Example 10, but utilizing the methyl ester of (5Z,13E)-(8R,9S,11R,12R,15R)-16,16-dimethyl-9,11,15-trihydroxyprostadienoic acid (see DOS 2,221,301), the product thus obtained is (5Z,13E)-(8R,9S,11R,12R,15R)-1-acetoxy-16,16-dimethylprostadiene-9,11,15-triol as a colorless oil.

IR (CHCl$_3$): 3600, 3430 (wide), 3000, 2940, 2860, 1730, 1255, 978 cm$^{-1}$.

EXAMPLE 16

(5Z,13E)-(8R,11R,12R,15S)-1-Acetoxy-11,15-dihydroxy-prostadien-9-one

At −45°, 1.2 ml. of N,N-diethyltrimethylsilylamine was added to a solution of 93 mg. of the 1-acetate prepared in accordance with Example 1 in 4 ml. of absolute acetone. The mixture was agitated for 6.5 hours at −40°. Thereafter, the mixture was diluted with 30 ml. of ether which had previously been cooled to −70°, shaken once with 5 ml. of ice-cooled sodium bicarbonate solution and twice with respectively 5 ml. of saturated sodium chloride solution, dried with sodium sulfate, and evaporated under vacuum. The 11,15-bis(-trimethylsilyl ether) obtained in this way was dissolved in 16 ml. of absolute methylene chloride and combined at +5° with a solution of 665 mg. of Collins reagent (preparation see Org. Syntheses, vol. 52, 5). The mixture was stirred for 10 minutes, diluted with 50 ml. of ether, filtered, and evaporated under vacuum. In order to split off the silyl ether blocking groups, the residue was stirred with a mixture of 9 ml. of methanol, 0.9 ml. of water, and 0.45 ml. of glacial acetic acid for 45 minutes at room temperature. The mixture was then diluted with 60 ml. of ether, shaken with 10 ml. of sodium bicarbonate solution and then twice with respectively 10 ml. of saturated sodium chloride solution, dried over magnesium sulfate, and evaporated under vacuum. After purification by preparative layer chromatography (ether/dioxane 9+1 as the eluent) on silica gel plates, the yield was 55 mg. of the title compound as a colorless oil.

TLC (ether/dioxane 9+1): Rf value 0.35.

IR (CHCl$_3$): 3600, 3400 (wide), 2998, 2960, 2930, 2860, 1738, 1730, 1602, 973 cm$^{-1}$.

NMR (CDCl$_3$): δ : 5.50-5.68 (2H,m); 5.22-5.44 (2H,m); 4.03 (2H,t,J=7 Hz); 3.93-4.18 (1H,m); 3.62-3.82 (1H,m); 2.05 (3H,s); 0.90 (3H,t,J=7 Hz).

EXAMPLE 17

(5Z,13E)-(8R,11R,12R,15S)-1-Isobutyryloxy-11,15-dihydroxyprostadien-9-one

Analogously to Example 16, the title compound is obtained as a colorless oil from the 1-isobutyrate prepared in accordance with Example 2.

IR (CHCl$_3$): 3600, 3430 (wide), 2998, 2938, 2860, 1740, 1725, 1160, 975 cm$^{-1}$.

EXAMPLE 18

(5Z,13E)-(8R,11R,12R,15S)-1-Benzoyloxy-11,15-dihydroxyprostadien-9-one

In analogy to Example 16, the title compound is produced as a colorless oil from the 1-benzoate prepared in accordance with Example 3.

IR (CHCl$_3$): 3600, 3425 (wide), 3000, 2940, 2860, 1740, 1712, 1600, 1278, 973 cm$^{-1}$.

EXAMPLE 19

(5Z,13E)-(8R,11R,12R,15S)-1-Decanoyloxy-11,15-dihydroxyprostadien-9-one

Analogously to Example 16, the title compound is produced as a colorless oil from the 1-decanoate prepared as set forth in Example 5.

IR (CHCl$_3$): 3600, 3430 (wide), 3000, 2930, 2860, 1738, 1730, 970 cm$^{-1}$.

EXAMPLE 20

(5Z,13E)-(8R,11R,12R,15S)-1-Butyryloxy-11,15-dihydroxyprostadien-9-one

Analogously to Example 16, the title compound is obtained as a colorless oil from the 1-butyrate produced as disclosed in Example 4.

IR (CHCl$_3$): 3600, 3430 (wide), 3000, 2930, 2860, 1738 (wide), 974 cm$^{-1}$.

EXAMPLE 21

(5Z,13E)-(8R,11R,12R,15S)-1-[(Methoxy)-acetoxy]-11,15-dihydroxyprostadien-9-one

In analogy to Example 16, the title compound is prepared in the form of a colorless oil from the 1-methoxyacetate produced in accordance with Example 6.

IR (CHCl$_3$): 3600, 3440 (wide), 3000, 2933, 2865, 1740 (wide), 975 cm$^{-1}$.

EXAMPLE 22

(5Z,13E)-(8R,11R,12R,15S)-1-Acetoxy-11,15-dihydroxy-1-methylprostadien-9-one

Analogously to Example 16, the title compound is obtained as a colorless oil from the 1-methyl-1-acetate produced as set forth in Example 7.

IR (CHCl$_3$): 3600, 3430 (wide), 3000, 2930, 2860, 1738, 1727, 1255, 978 cm$^{-1}$.

EXAMPLE 23

(5Z,13E)-(8R,11R,12R,15S)-1-Acetoxy-11,15-dihydroxy-1,1-dimethylprostadien-9-one Analogously to Example 16, the title compound is obtained as a colorless oil from the 1,1-dimethyl-1-acetate produced analogously to Example 8.

IR (CHCl$_3$): 3595, 3410 (wide), 2960, 2930, 2860, 1738, 1720, 1600, 1265, 970 cm$^{-1}$.

EXAMPLE 24

(5Z,13E)-(8R,11R,12R,15S)-1-Acetoxy-11,15-dihydroxy-15-methylprostadien-9-one

Analogously to Example 16, the title compound is produced as a colorless oil from the 1-acetate prepared in accordance with Example 9.

IR (CHCl$_3$): 3600, 3430 (wide), 2930, 2860, 1738 (wide), 1245, 975 cm$^{-1}$.

EXAMPLE 25

(5Z,13E)-(8R,11R,12R,15R)-1-Acetoxy-11,15-dihydroxy-16-phenoxy-17,18,19,20-tetranorprostadien-9-one In analogy to Example 16, the title compound is prepared as a colorless oil from the 1-acetate produced as set forth in Example 10.

IR (CHCl$_3$): 3600, 3440 (wide), 2940, 2860, 1738, 1728, 1600, 1588, 1495, 1240, 975 cm$^{-1}$.

EXAMPLE 26

(5Z,13E)-(8R,11R,12R,15R)-1-Acetoxy-11,15-dihydroxy-16-(3-trifluoromethylphenoxy)-17,18,19,20-tetranorprostadien-9-one Analogously to Example 16, the title compound is produced as a colorless oil from the 1-acetate prepared according to Example 11.

IR (CHCl$_3$): 3600, 3430 (wide), 3000, 2940, 2860, 1738, 1730, 1600, 1595, 1490, 1240, 975 cm$^{-1}$.

EXAMPLE 27

(5Z,13E)-(8R,11R,12R,15R)-1-Acetoxy-11,15-dihydroxy-16-(4-chlorophenoxy)-17,18,19,20-tetranorprostadien-9-one In analogy to Example 16, the title compound is obtained as a colorless oil from the 1-acetate produced as disclosed in Example 12.

IR (CHCl$_3$): 3600, 3430 (wide), 3000, 2945, 2860, 1738, 1730, 1600, 1583, 1492, 1245, 976, 875, 830 cm$^{-1}$.

EXAMPLE 28

(5Z,13E)-(8R,11R,12R,15S)-1-Acetoxy-11,15-dihydroxy-17-phenyl-18,19,20-trinorprostadien-9-one Analogously to Example 16, the title compound is produced as a colorless oil from the 1-acetate prepared as set forth in Example 13.

IR (CHCl$_3$): 3600, 3400 (wide), 3000, 2960, 2860, 1738, 1731, 1600, 1250, 975 cm$^{-1}$.

EXAMPLE 29

(5Z,13E)-(8R,11R,12R,15S)-1-Acetoxy-15-hydroxy-11-methylprostadien-9-one

Analogously to Example 16, the title compound is obtained as a colorless oil from the 1-acetate prepared as disclosed in Example 14.

IR (CHCl$_3$): 3600, 3430 (wide), 3000, 2950, 2860, 1738, 1725, 1260, 978 cm$^{-1}$.

EXAMPLE 30

(5Z,13E)-(8R,11R,12R,15R)-1-Acetoxy-11,15-dihydroxy-16,16-dimethylprostadien-9-one In analogy to Example 16, the title compound is produced in the form of a colorless oil from the 1-acetate produced in Example 15.

IR (CHCl$_3$): 3600, 3420 (wide), 2940, 2860, 1738, 1730, 1255, 975 cm$^{-1}$.

EXAMPLE 31

(5Z,13E)-(8R,12S,15S)-1-Acetoxy-15-hydroxy-prosta-5,10,13-trien-9-one

A mixture of 100 mg. of the 1-acetate produced according to Example 16 was stirred for 14 hours at 60° with 8 ml. of a 90% aqueous acetic acid. The mixture was then evaporated under vacuum and the residue was purified by preparative layer chromatography (ether) on silica gel plates, thus obtaining 68 mg. of the title compound as a colorless oil.

IR (CHCl$_3$): 3600, 3460 (wide), 3000, 2960, 2935, 2860, 1735, 1702, 1240, 970 cm$^{-1}$.

NMR (CDCl$_3$): δ : 7.45 (1H,dd,J=6+2.5 Hz); 6.13 (1H,dd,J=6 +2 Hz); 4.08 (2H,t,J=6.5 Hz); 8.05 (3H,s); 0.90 (3H,t,J=6.5 Hz).

EXAMPLE 32

(5Z,13E)-(8R,12S,15S)-1-Acetoxy-15-hydroxy-15-methylprosta-5,10,13-trien-9-one

A mixture of 95 mg. of the 1-acetate prepared in accordance with Example 24 and 8 ml. of a 90% aqueous acetic acid was agitated for 16 hours at 60°. Then, the mixture was evaporated under vacuum and the residue was purified by preparative layer chromatography (ether) on silica gel plates, thus obtaining 60 mg. of the title compound as a colorless oil.

IR (CHCl$_3$): 3600, 3450 (wide), 3000, 2960, 2935, 2860, 1735, 1702, 1240, 974 cm$^{-1}$.

EXAMPLE 33

(5Z,13E)-(1RS,8R,9S,11R,12R,15S)-1,9,11,15-Tetraacetoxy-1-methylprostadiene

A mixture of 530 mg. of (5Z,13E)-(1RS,8R,9S,11R,12R,15S)-1-methyl-9,11,15-tris(tetrahydropyran-2-yloxy)prostadien-1-ol (prepared in accordance with Example 7[b]) and 20 ml. of an acetic acid/water/tetrahydrofuran mixture (65/35/10) was stirred for 14 hours at room temperature under argon. The mixture was then evaporated under vacuum and the residue purified by chromatography over silica gel. With ether/isopropanol (9+1), 210 mg. of (5Z,13E)-(1RS,8R,11R,12R,15S)-1,9,11,15-tetrahydroxy-1-methylprostadiene was obtained as a colorless oil.

TLC (ether/dioxane 7+3): Rf value 0.21.

The tetrol produced in this manner was allowed to stand for 14 hours with a mixture of 0.2 ml. of acetic anhydride and 0.8 ml. of pyridine at room temperature. After evaporation, the tetraacetate was purified by filtration over silica gel. With ether/hexane (8+2), 280 mg. of the title compound was produced as a colorless oil.

IR (CHCl$_3$): 3000, 2960, 2935, 2860, 1735, 1240, 975 cm$^{-1}$.

EXAMPLE 34

(5Z,13E)-(8R,9S,11R,12R,15R)-1-(3-Carboxypropionyloxy)-16,16-dimethylprostadiene-9,11,15-triol At room temperature, 200 mg. of (5Z,13E)-(8R,9S,11R-12R,15R)-1-(3-carboxypropionyl)-9-tribenzylsilyloxy-11,15-bis(tetrahydropyran-2-yloxy)prostadiene was agitated in 10 ml. of a mixture of glacial acetic acid/water/tetrahydrofuran (65/35/10) for 14 hours. The mixture was evaporated under vacuum and the residue purified by column chromatography on silica gel. With methylene chloride/isopropanol (7+3), 72 mg. of the title compound was obtained as a colorless oil.

IR (CHCl$_3$): 3600, 2940, 1728, 976 cm$^{-1}$.

The starting material for the above reaction was prepared as follows:

3.6 g. of 16,16-dimethylprostaglandin-F$_{2\alpha}$-methyl ester 11,15-bis(tetrahydropyranyl)ether (produced according to DOS 2,221,301 from the acid with diazomethane), dissolved in 54 ml. of pyridine, was combined with 2.82 g. of tribenzylsilyl chloride and agitated under argon for 3 hours at 48°. The solvent was distilled off under vacuum at 15 torr [mm. Hg] and the residue chromatographed on silica gel. With ether/pentane mixtures, 4.2 g. of the corresponding 9-tribenzylsilyl ether was eluted as a colorless oil.

4.2 g. of the silyl ether in 180 ml. of absolute ether was combined at 20° in incremental portions with 1.20 g. of lithium aluminum hydride, agitated for 3 hours at 20°, the excess reagent was destroyed by the dropwise addition of ethyl acetate, and 2.8 ml. of water was added thereto. The mixture was agitated for 1 hour, filtered, and evaporated under vacuum. Of the thus-obtained 1-alcohol, 830 mg. was dissolved in 1.5 ml. of pyridine, and 120 mg. of succinic anhydride was added. The mixture was stirred for 16 hours at 20° and then combined with 10 ml. of water. The reaction mixture was agitated for 15 minutes, extracted with ether, the extract shaken with brine, dried over magnesium sulfate, and evaporated to dryness under vacuum. After filtration over silica gel with methylene chloride, 530 mg. of (5Z,13E)-(8R,9S,11R,12R,15R)-1-(3-carboxypropionyl)-9-tribenzylsilyloxy-11,15-bis(tetrahydropyran-2-yloxy)prostadiene was obtained as a colorless oil.

IR (CHCl$_3$): 2940, 1728, 1600, 1495, 1165, 1020, 978 cm$^{-1}$.

EXAMPLE 35

(5Z,13E)-(8R,11R,12R,15R)-1-(3-Carboxypropionyloxy)-11,15-dihydroxy-16,16-dimethylprostadien-9-one At 40°, 265 mg. of (5Z,13E)-(8R,11R,12R,15R)-1-(3-carboxypropionyloxy)-16,16-dimethyl-11,15-bis(tetrahydropyran-2-yloxy)-prostadien-9-one was agitated for 5 hours with 7 ml. of a mixture of glacial acetic acid/water/tetrahydrofuran (65/35/10). The mixture was then evaporated to dryness under vacuum. The oily residue was purified by chromatography on silica gel. With methylene chloride/isopropanol (8+2), 90 mg. of the title compound was obtained as a colorless oil.

IR (CHCl$_3$): 3600, 2940, 1738 (shoulder), 1728, 978 cm$^{-1}$.

The starting material was prepared as follows:

750 mg. of (5Z,13E)-(8R,9S,11R,12R,15R)-1-(3-carboxypropionyl)-9-tribenzylsilyloxy-11,15-bis(tetrahydropyran-2-yloxy)prostadiene and 223 mg. of tetrabutylammonium fluoride was stirred in 60 ml. of tetrahydrofuran for 2 hours at 0°. The mixture was diluted with water, acidified with 10% citric acid to pH 5, extracted with ether, the organic extract shaken with brine, dried over magnesium sulfate, and evaporated to dryness under vacuum. Filtration over silica gel with ether yielded 430 mg. of the 9-hydroxy compound as a colorless oil.

IR (CHCl$_3$): 3500 (wide), 2940, 1728, 1468, 1452, 1440, 1125, 1020, 978 cm$^{-1}$.

300 mg. of the above-produced 9-hydroxy compound was dissolved in 7 ml. of acetone, and 0.25 ml. of Jones reagent was added dropwise at −20°. After 25 minutes, the excess reagent was destroyed by adding isopropanol; the mixture was diluted with ether and shaken with brine until neutral. After drying over magnesium sulfate and evaporation, 270 mg. of the 9-keto compound was obtained as a colorless oil.

IR (CHCl$_3$): 3600 (wide), 2940, 1738 (shoulder), 1730, 978 cm$^{-1}$.

EXAMPLE 36

(5Z,10Z,13E)-(8R,12S,15R)-1-(3-Carboxypropionyloxy)-15-hydroxy-16,16-dimethyl-5,10,13-prostatrien-9-one A mixture of 200 mg. of (5Z,13E)-(8R,11R,12R,15R)-1-(3-carboxypropionyloxy)-11,15-dihydroxy-16,16-dimethylprostadien-9-one and 15 ml. of 90% acetic acid was agitated for 16 hours at 60°. The mixture was then evaporated under vacuum and the residue purified by preparative layer chromatography (silica gel, methylene chloride/isopropanol 9+1), thus obtaining 105 mg. of the title compound as a colorless oil.

IR (CHCl$_3$): 3600, 3500 (wide), 2940, 1730, 1602, 976 cm$^{-1}$.

EXAMPLE 37

(5Z,13E)-(8R,9S,11R,12R,15S)-1-(N-Methylcarbamoyloxy)-5,13-prostadiene-9,11,15-triol In succession, 1.2 ml. of methyl isocyanate and 3 drops of triethylamine were added to a solution of 300 mg. of the 1-alcohol obtained according to Example 37(b) in 5 ml. of absolute tetrahydrofuran. The mixture was allowed to stand overnight at room temperature, evaporated to dryness under vacuum, and the residue purified by filtering over silica gel with ether/pentane (1+1), thus obtaining 305 mg. of the corresponding urethane as a colorless oil.

IR (CHCl$_3$): 3470, 2943, 1700, 1650, 1020, 975 cm$^{-1}$.

At 50°, 250 mg. of (5Z,13E)-(8R,9S,11R,12R,15S)-1-(N-methylcarbamoyloxy)-11,15-bis(tetrahydropyran-2-yloxy)-9-tribenzylsilyloxy-5,13-prostadiene was stirred for 5 hours in 15 ml. of a mixture of glacial acetic acid/water/tetrahydrofuran (65/35/10). The mixture was evaporated under vacuum and the residue purified by chromatography on silica gel with ether/dioxane (7+3), thus obtaining 105 mg. of the title compound as a colorless oil.

IR (CHCl$_3$): 3605, 3470, 2935, 1700, 1650, 1512, 1080, 972, 947 cm$^{-1}$.

NMR (CDCl$_3$): δ: 5.3-5.6 (4H,m) — olefinic protons 3.8-4.3 (5H,m) — carbinol protons and —CH$_2$—CH$_2$—O

| | |
|---|---|
| 2.85 (d,7 Hz) <br> 2.78 (d,7 Hz) | —NH—CH$_3$ |
| 0.88 (t,7 Hz, 3H) | —CH$_2$—CH$_3$ |

The starting material for the above reaction was prepared as set forth below:

37(a) 1.80 g. of prostaglandin-F$_{2\alpha}$-methyl ester-11,15-bis(tetrahydropyranyl)ether (obtained from the corresponding acid, see J. Amer. Chem. Soc. 91, 5675 [1969], with diazomethane), dissolved in 25 ml. of pyridine, was combined with 1.40 g. of tribenzylsilyl chloride and agitated for 5 hours at 50° under argon. After the solvent had been distilled off under vacuum, the oily residue was chromatographed on silica gel with ether/pentane mixtures, thus obtaining 2.05 g. of the corresponding 9-tribenzylsilyl ether as a colorless oil.

37(b) 2.05 g. of the silyl ether in 80 ml. of absolute ether was combined at room temperature in incremental portions with 0.5 g. of lithium aluminum hydride. The reaction mixture was agitated for 2 hours at 20°, the excess reagent was decomposed with ethyl acetate, and 1.2 ml. of water was added. The mixture was agitated for 1 hour at 20°, filtered, and evaporated under vacuum, thus producing 1.95 g. of (5Z,13E)-(8R,9S,11R,12R,15S)-11,15-bis(tetrahydropyran-2-yloxy)-9-tribenzylsilyloxy-5,13-prostadien-1-ol, which was completely uniform as determined by thin-layer chromatography.

The IR spectrum (in chloroform) did not show any carbonyl oscillation any more.

EXAMPLE 38

(5Z,13E)-(8R,11R,12R,15S)-1-(N-Methylcarbamoyloxy)-11,15-dihydroxy-5,13-prostadien-9-one At 40°, 300 mg. of (5Z,13E)-(8R,11R,12R,15S)-1-(N-methylcarbamoyloxy)-11,15-bis(tetrahydropyran-2-yloxy)-5,13-prostadien-9-one was agitated with 9 ml. of a mixture of glacial acetic/water/tetrahydrofuran (65/35/10) for 6 hours. The mixture was then evaporated to dryness under vacuum. After purifying the residue by chromatography on silica gel (ether/ethyl acetate 7+3), 145 mg. of the title compound was obtained as a colorless oil.

IR (CHCl$_3$): 3605, 3470, 2940, 1735, 1700, 1650, 1512, 1085, 972, 948 cm$^{-1}$.

The starting material for the above reaction was produced as follows:

38(a) A solution of 370 mg. of the urethane prepared according to Example 37 and 110 mg. of tetrabutylammonium fluoride in 30 ml. of tetrahydrofuran was agitated for 2 hours at 0°, diluted with water, extracted with ether, the organic extract was shaken with brine, dried over magnesium sulfate, and evaporated to dryness under vacuum. After filtration over silica gel with ether, 205 mg. of (5Z,13E)-(8R,9S,11R,12R,15S)-1-(N-methylcarbamoyloxy)-11,15-bis(tetrahydropyran-2-yloxy)-5,13-prostadien-9-ol was obtained as a colorless oil.

38(b) At −20°, 0.25 ml. of Jones reagent was added dropwise to a solution of 290 mg. of the 9-hydroxy compound obtained as set out above in 8 ml. of acetone. The mixture was stirred for 25 minutes at −20°, and the excess reagent was destroyed by adding isopropanol, diluted with ether, and shaken with brine until neutral. After drying over magnesium sulfate and evaporation, 265 mg. of (5Z,13E)-(8R,11R,12R,15S)-1-(N-methylcarbamoyloxy)-11,15-bis(tetrahydropyran-2-yloxy)-5,13-prostadien-9-one was obtained as a colorless oil.

IR (CHCl$_3$): 3470, 2945, 1735, 1700, 1650, 1080, 972, 948 cm$^{-1}$.

EXAMPLE 39

(5Z,13E)-(8R,12S,15S)-1-(N-Methylcarbamoyloxy)-15-hydroxy-5,10,13-prostatrien-9-one 250 mg. of the PG E derivative obtained according to Example 38 was agitated in 16 ml. of 90% acetic acid for 16 hours at 60°, then evaporated under vacuum, and the residue purified by preparative layer chromatography (silica gel, ether), thus obtaining 165 mg. of the title compound as a colorless oil.

IR (CHCl$_3$): 3600, 3500 (wide), 2940, 1700, 1602, 978 cm$^{-1}$.

EXAMPLE 40

(5Z,13E)-(8R,9S,11R,12R,15S)-1-[(N-Methanesulfonyl)-carbamoyloxy]-5,13-prostadiene-9,11,15-triol At 0°, 145 mg. of methanesulfonyl isocyanate was added to a solution of 405 mg. of the 1-alcohol obtained according to Example 37(b) in 10 ml. of absolute toluene. The mixture was agitated for 1 hour at 20-25°, combined with water, extracted with ether, the extract washed with brine, dried over magnesium sulfate, and evaporated under vacuum. After filtering the residue over silica gel with methylene chloride, 390 mg. of (5Z,13E)-(8R,9S,11R,12R,15S)-1-[(N-methanesulfonyl)-carbamoyloxy]-11,15-bis(tetrahydropyran-2-yloxy)-9-tribenzoylsilyloxy-5,13-prostadiene was produced as a colorless oil.

From 300 mg. of this compound, 120 mg. of the title compound was obtained analogously to Example 37 as a colorless oil.

IR (CHCl$_3$): 3600, 3380, 1720, 1400, 1346, 1020, 975 cm$^{-1}$.

EXAMPLE 41

(5Z,13E)-(8R,11R,12R,15S)-1-[(N-Methanesulfonyl)-carbamoyloxy]-11,15-dihydroxy-5,13-prostadien-9-one Analogously to Example 38, 112 mg. of the title compound was obtained in the form of a colorless oil from 250 mg. of (5Z,13E)-(8R,11R,12R,15S)-1-[(N-methanesulfonyl)-carbamoyloxy]-11,15-bis(tetrahydropyran-2-yloxy)-5,13-prostadien-9-one.

IR (CHCl$_3$): 3600, 3400, 2940, 1735 (shoulder), 1720, 1400, 1345, 1020, 976 cm$^{-1}$.

The starting material for the above reaction was prepared as follows:

41(a) Analogously to Example 38(a), 400 mg. of the 9-tribenzylsilyloxy compound prepared according to Example 4 and 120 mg. of tetrabutylammonium fluoride yielded 210 mg. of (5Z,13E)-(8R,9S,11R,12R,15S)-1-[(N-methanesulfonyl)-carbamoyloxy]-11,15-bis(tetrahydropyran-2-yloxy)-5,13-prostadien-9-ol as a colorless oil.

41(b) In analogy to Example 38(b), 210 mg. of the above-produced compound and 0.2 ml. of Jones reagent yielded 170 mg. of (5Z,13E)-(8R,11R,12R,15S)-1-[(N-methanesulfonyl)-carbamoyloxy]-11,15-bis(tetrahydropyran-2-yloxy)-5,13-prostadien-9-one as a colorless oil.

EXAMPLE 42

(5Z,13E)-(8R,12S,15S)-1-[(N-Methanesulfonyl)-carbamoyl-oxy]-15-hydroxy-5,10,13-prostatrien-9-one At 60°, 200 mg. of the PG E derivative obtained according to Example 41 was agitated in 12 ml. of 90% acetic acid for 16 hours. The mixture was evaporated under vacuum and the residue purified by preparative layer chromatography (silica gel, methylene chloride/isopropanol 9+1), thus obtaining 105 mg. of the title compound as a colorless oil.

IR (CHCl$_3$): 3600, 3500, 2944, 1710, 1603, 978 cm$^{-1}$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Prostane derivatives of the formula

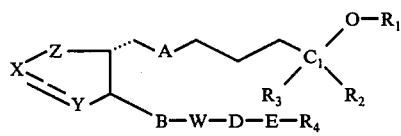

wherein $R_1$ is the monovalent acyl radical of a hydrocarbon dicarboxylic acid of up to 15 carbon atoms; $R_2$ and $R_3$ each are hydrogen or alkyl of 1–4 carbon atoms;

A is —CH$_2$—CH$_2$—, cis—CH=CH— or trans—CH=CH—;

B is —CH$_2$—CH$_2$—, trans—CH=CH—, —C≡C— or

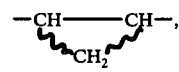

wherein the methylene group is in either the α- or β- position;

W is hydroxymethylene, carbonyl, or

wherein the OH—group is in either the α- or β- position;

D and E together form a covalent bond, or D is a straight-chain or branched alkylene group of 1–5 carbon atoms or a —C≡C—group and E is oxygen, sulfur or a covalent bond;

$R_4$ is alkyl of 1–10 carbon atoms or cycloalkyl of 4–10 carbon atoms;

Z is carbonyl or hydroxymethylene;

X---Y is

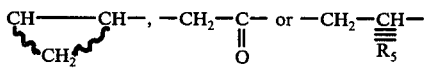

wherein $R_5$ is lower alkyl or hydroxyl when Z is hydroxymethylene, and X---Y is —CH=CH— or

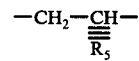

wherein $R_5$ is lower alkyl or hydroxyl when Z is carbonyl.

2. A compound according to claim 1, wherein at least one of $R_2$ and $R_3$ is methyl or ethyl.

3. A compound according to claim 1, wherein $R_2$ and $R_3$ are hydrogen.

4. A compound according to claim 1, wherein $R_1$ is the acyl radical of succinic or adipic acid.

5. (5Z,13E)-(8R,11R,12R,15R)-1-(3-carboxypropionyloxy-11,15-dihydroxy-16,16-dimethylprostadien-9-one; (5Z,10Z,13E)-(8R,12R,15R)-1-(3-carboxypropionyloxy)-15-hydroxy-16,16-dimethyl-5,10,13-prostatrien-9-one, a compound of claim 1.

6. (5Z,13E)-(8R,9S,11R,12R,15R)-1-(3-carboxypropionyloxy)-16,16-dimethylprostadiene-9,11,15-triol, a compound of claim 1.

7. (5Z,13E)-(8R,11R,12R,15R)-1-(3-Carboxypropionyloxy)-11,15-dihydroxy-16,16-dimethylprostandien-9-one, a compound of claim 1.

8. A pharmaceutical composition comprising an abortion-inducing amount of a compound according to claim 1 per unit dosage, in admixture with a pharmaceutically acceptable carrier.

9. In a method for inducing abortion in pregnant mammals, the improvement which comprises administering a safe and effective amount of a compound according to claim 1 to a pregnant mammal effective to induce abortion therein.

* * * * *